US012716046B2

(12) United States Patent
Okamoto et al.

(10) Patent No.: US 12,716,046 B2
(45) Date of Patent: Aug. 25, 2026

(54) CELL DETACHING APPARATUS AND CELL DETACHING METHOD

(71) Applicant: CANON KABUSHIKI KAISHA, Tokyo (JP)

(72) Inventors: Takuji Okamoto, Tokyo (JP); Takayuki Tsukimoto, Kanagawa (JP); Norihiro Suzuki, Kanagawa (JP)

(73) Assignee: Canon Kabushiki Kaisha, Tokyo (JP)

(*) Notice: Subject to any disclaimer, the term of this patent is extended or adjusted under 35 U.S.C. 154(b) by 686 days.

(21) Appl. No.: 18/162,463

(22) Filed: Jan. 31, 2023

(65) Prior Publication Data

US 2023/0242858 A1 Aug. 3, 2023

(30) Foreign Application Priority Data

Jan. 31, 2022 (JP) ................................ 2022-013182
Dec. 9, 2022 (JP) ................................ 2022-197059

(51) Int. Cl.
*C12M 1/26* (2006.01)
*C12M 1/00* (2006.01)
(Continued)

(52) U.S. Cl.
CPC ............ *C12M 33/08* (2013.01); *C12M 23/22* (2013.01); *C12M 31/10* (2013.01); *C12M 41/12* (2013.01);
(Continued)

(58) Field of Classification Search
None
See application file for complete search history.

(56) References Cited

U.S. PATENT DOCUMENTS 3,365,945 A * 1/1968 Parks ....................... G01N 9/02 73/61.43
2013/0084622 A1* 4/2013 Ram ...................... C12M 41/40 435/252.8

(Continued)

FOREIGN PATENT DOCUMENTS

JP 2008092857 A 4/2008
JP 2008178304 A 8/2008

(Continued)

OTHER PUBLICATIONS

Kurashina et al., "Effective cell collection method using collagenase and ultrasonic vibration", Biomicrofluidics 8, 054118 (2014) (Year: 2014).*

(Continued)

*Primary Examiner* — Henry H Nguyen
(74) *Attorney, Agent, or Firm* — Canon U.S.A., Inc. IP Division

(57) ABSTRACT

There is provided a cell detaching apparatus for detaching cells from a base material by applying an ultrasonic vibration via an acoustic matching liquid, with reduced variations of the vibration transmitted to the cells during application of the ultrasonic vibration. A cell detaching apparatus for detaching cells placed on a base material floating on an acoustic matching liquid, from the base material includes a holding unit configured to hold the acoustic matching liquid, a detaching unit configured to detach the cells from the base material by applying an ultrasonic vibration to the cells through the acoustic matching liquid, and a control unit configured to perform control to maintain a constant height of a fluid level of the acoustic matching liquid held by the holding unit with respect to the base material.

10 Claims, 41 Drawing Sheets

(51) Int. Cl.

| | |
|---|---|
| ***C12M 1/34*** | (2006.01) |
| ***C12N 13/00*** | (2006.01) |

(52) U.S. Cl.

CPC ............. *C12M 41/44* (2013.01); *C12N 13/00* (2013.01); *C12N 2509/00* (2013.01)

(56) References Cited

U.S. PATENT DOCUMENTS

| | | | | |
|---|---|---|---|---|
| 2014/0370492 | A1* | 12/2014 | Yasuda | B01L 7/52 435/286.1 |
| 2017/0015963 | A1* | 1/2017 | Ott | A61K 35/42 |
| 2019/0218500 | A1* | 7/2019 | Takimoto | G16B 50/30 |
| 2021/0362145 | A1* | 11/2021 | Kim | B06B 1/0696 |

FOREIGN PATENT DOCUMENTS

| | | | |
|---|---|---|---|
| JP | 2008259490 | A | 10/2008 |
| JP | 2011115080 | A | 6/2011 |
| JP | 2012217443 | A | 11/2012 |
| JP | 2019170305 | A | 10/2019 |
| WO | 2016047368 | A1 | 3/2016 |

OTHER PUBLICATIONS

Imashiro et al., "Detachment of cell sheets from clinically ubiquitous cell culture vessels by ultrasonic vibration", Nature Scientific Reports, 10, 9468 (2020) (Year: 2020).*

* cited by examiner

ALTERNATING SIGNAL GENERATION CONTROL CIRCUIT
105b
101
106
109
105a
104
110
100
111
112
103
108

1
COMMUNICATION AMPLIFICATION AND PROCESSING CIRCUIT
109
106
118
120
110
119
122
117
107
102
101
100
100a
100b
111
105
114
103
121
108

(1) VIBRATED (2) NOT VIBRATED

COMMUNICATION AMPLIFICATION AND PROCESSING CIRCUIT
FLUID LEVEL ADJUSTMENT
100
100a
100b
101
102
103
105
106
107
108
109
110
114
117
118
119
120
121
122

VIBRATION TRANSMISSION FLUID IN STORAGE TUB
103
102
VIBRATION TRANSMISSION FLUID IN VIBRATION TUB
107
INITIAL FLUID POSITION (STEP POSITION)
120
101
ZC
YC
XC
(1) MOVED DOWN
FLUID UPPER LIMIT POSITION (UPPER LIMIT INDICATOR LINE)
100
(2) SUNK
FLUID LOWER LIMIT POSITION (LOWER LIMIT INDICATOR FORM)
110
114
(3) MOVED UP

HIGH
LOW
125
126
126
127
1
128a
128b
129
130

INSTALLATION SURFACE
SAME POSITION
217
215
202
110
DISH HOLDING SURFACE
216
100
ROTATION LOCUS
1

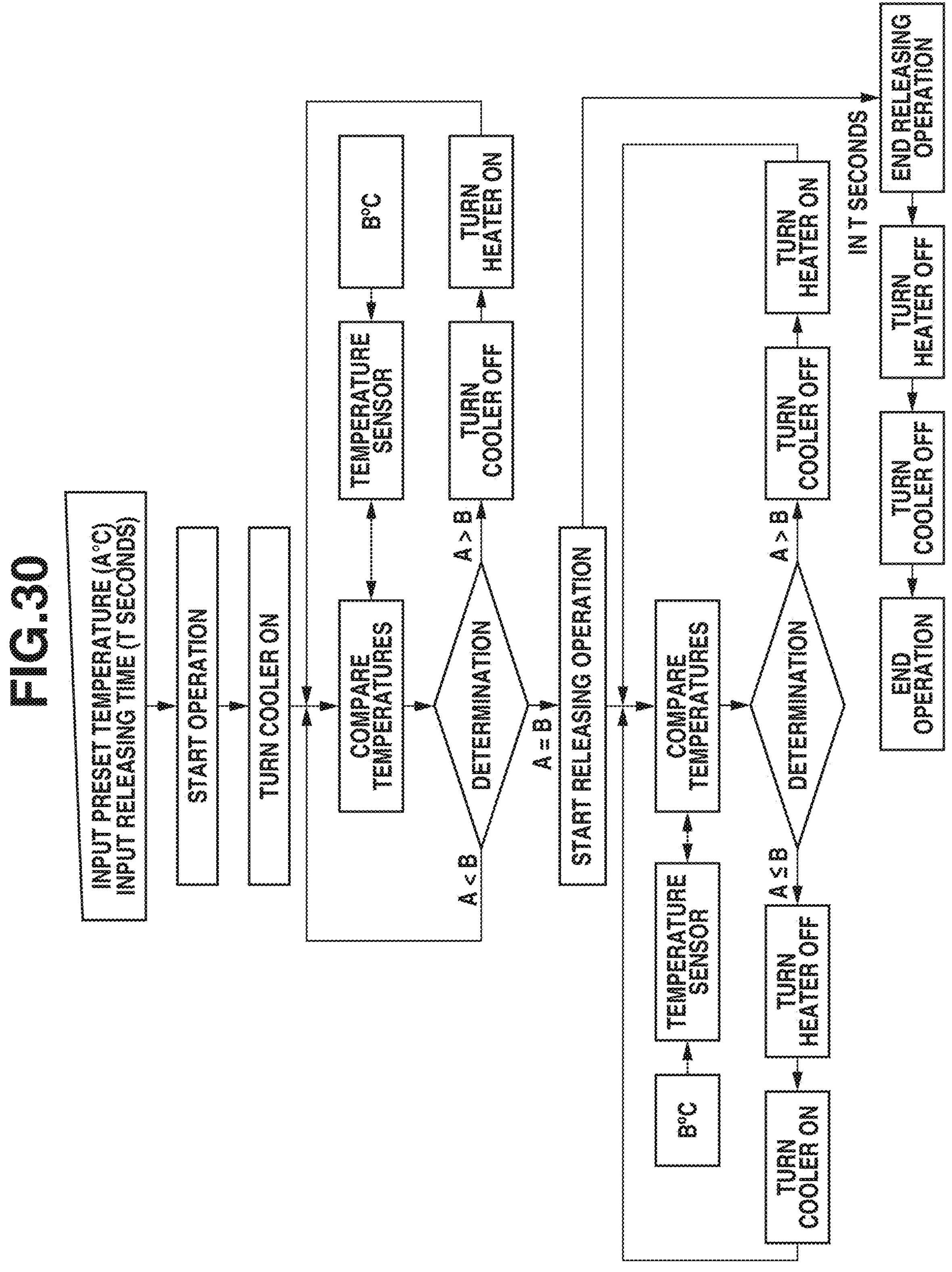
FIG.30
INPUT PRESET TEMPERATURE (A°C)
INPUT RELEASING TIME (T SECONDS)
START OPERATION
TURN COOLER ON
COMPARE TEMPERATURES
TEMPERATURE SENSOR
B°C
DETERMINATION
A < B
A > B
TURN COOLER OFF
TURN HEATER ON
A = B
START RELEASING OPERATION
COMPARE TEMPERATURES
TEMPERATURE SENSOR
B°C
DETERMINATION
A ≤ B
TURN HEATER OFF
TURN COOLER ON
A > B
TURN COOLER OFF
TURN HEATER ON
IN T SECONDS
END RELEASING OPERATION
TURN HEATER OFF
TURN COOLER OFF
END OPERATION

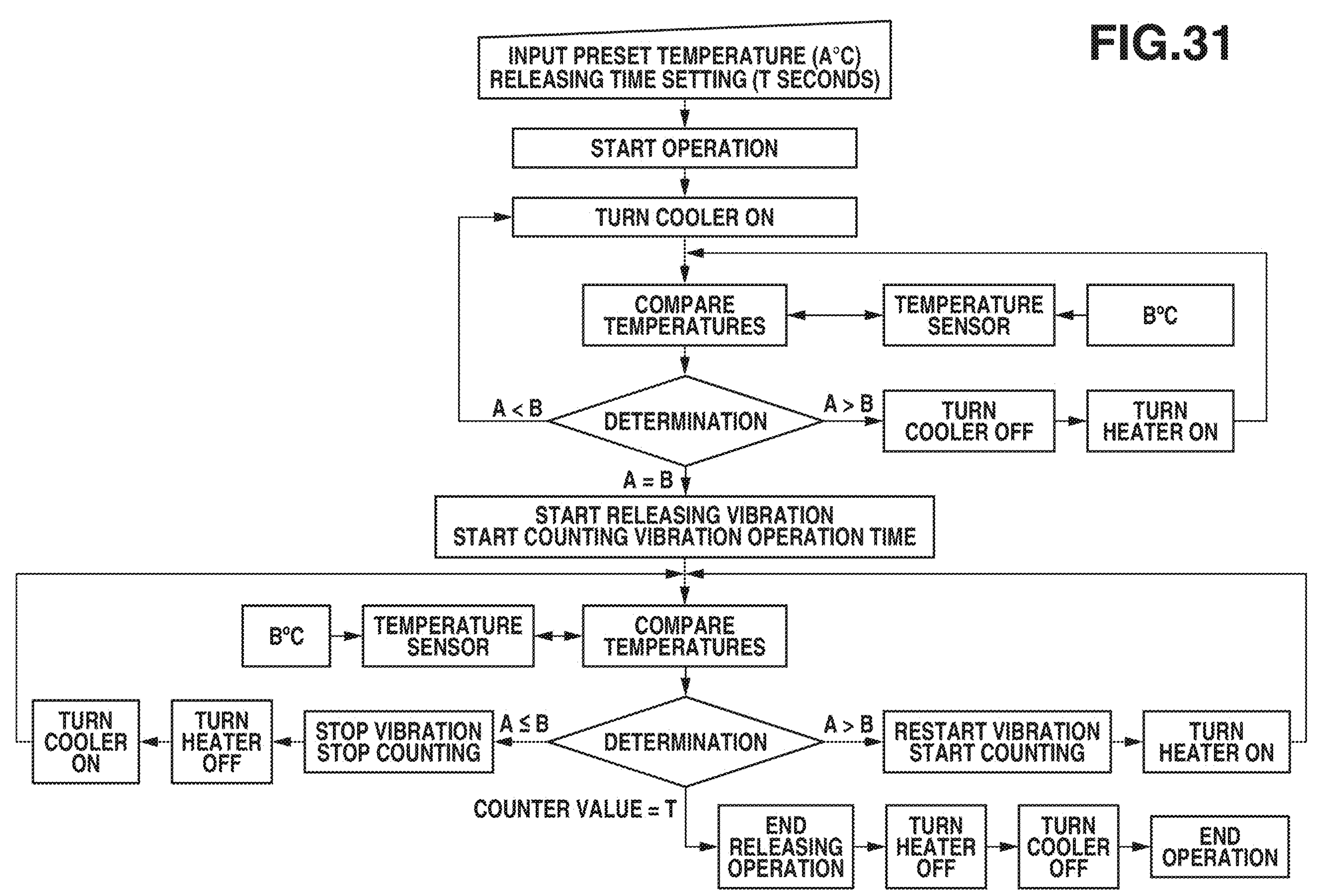
FIG.31
INPUT PRESET TEMPERATURE (A°C)
RELEASING TIME SETTING (T SECONDS)
START OPERATION
TURN COOLER ON
COMPARE TEMPERATURES
TEMPERATURE SENSOR
B°C
DETERMINATION
A < B
A > B
TURN COOLER OFF
TURN HEATER ON
A = B
START RELEASING VIBRATION
START COUNTING VIBRATION OPERATION TIME
B°C
TEMPERATURE SENSOR
COMPARE TEMPERATURES
DETERMINATION
A ≤ B
A > B
STOP VIBRATION
STOP COUNTING
TURN HEATER OFF
TURN COOLER ON
RESTART VIBRATION
START COUNTING
TURN HEATER ON
COUNTER VALUE = T
END RELEASING OPERATION
TURN HEATER OFF
TURN COOLER OFF
END OPERATION 239
102

100
100b 100a
CULTURE SOLUTION
CELLS
110
227
239
102

CELL IMAGE
DISH IMAGE
REFLECTED LED
240
124
LED CENTER LIGHT
100
100a 100b
225
123
CELLS
102
CULTURE SOLUTION
117

CELL IMAGE
DISH IMAGE
240
124
100
100a 100b
225
123
CELLS
102
CULTURE SOLUTION
117

CELL DETACHING APPARATUS AND CELL DETACHING METHOD

BACKGROUND OF THE DISCLOSURE

Field of the Disclosure

The present disclosure relates to a cell detaching apparatus and a cell detaching method.

Description of the Related Art

In the medical field, cells are cultured on the bottom surface of a vessel such as a cultural plate or a dish for the purpose of treatment, research, and development. However, since cells are bonded to the bottom surface of the vessel, it is necessary to detach and take out sample cells from the vessel in which the cells have been cultured.

Examples of methods for detaching such cells from the vessel include a method for using a detaching enzyme or a chemical acting on the cell membrane, a method for using a temperature-responsive polymer, and a method for applying a vibration energy to the cells by using an incident ultrasonic wave. International Patent Publication No. WO 2016-047368 discusses a cell detaching apparatus in which an ultrasonic wave emission unit is disposed separately from the outer surface of a vessel, and the ultrasonic wave emission unit and a processing target region on the outer surface of the vessel are connected with an ultrasonic wave transmission substance. In the cell detaching apparatus discussed in International Patent Publication No. WO 2016-047368, the ultrasonic wave emitted by the ultrasonic wave emission unit is incident on the processing target region via the ultrasonic wave transmission substance. Since the scattering in the air and the reflection on the outer surface of the vessel are restrained, the ultrasonic wave is incident on detaching target cells with high selectivity to detach the cells from the vessel.

The inventors have found an issue regarding the cell detaching apparatus discussed in International Patent Publication No. WO 2016-047368. More specifically, the cell detaching apparatus discussed in International Patent Publication No. WO 2016-047368 applies an ultrasonic wave in a fluid-tight state between the ultrasonic emission unit and the processing target region while supplying the ultrasonic wave transmission substance (fluid). However, in the configuration for applying an ultrasonic wave while supplying the ultrasonic wave transmission substance, the contact area between the ultrasonic wave transmission substance and the vessel with the cells placed therein is likely to change. As a result, the inventors have found that the vibration transmitted to the cells may change even without changing a drive condition of the ultrasonic emission unit.

If a vessel with the cells placed therein is disposed on a ultrasonic wave transmission substance stored in a vessel, the contact area between the ultrasonic wave transmission substance and the vessel is more unlikely to change than that in the configuration discussed in International Patent Publication No. WO 2016-047368. However, during application of the ultrasonic vibration to the cells, the vibration is also transmitted to the ultrasonic wave transmission substance, possibly changing the amount of the ultrasonic wave transmission substance.

SUMMARY OF THE DISCLOSURE

The present disclosure is directed to providing a cell detaching apparatus for detaching cells from a base material by applying an ultrasonic vibration via an acoustic matching liquid, with reduced variations of the vibration transmitted to the cells during application of the ultrasonic vibration.

According to an aspect of the present disclosure, a cell detaching apparatus for detaching cells placed on a base material floating on an acoustic matching liquid, from the base material includes a holding unit configured to hold the acoustic matching liquid, a detaching unit configured to detach the cells from the base material by applying an ultrasonic vibration to the cells through the acoustic matching liquid, and a control unit configured to perform control to maintain a constant height of a fluid level of the acoustic matching liquid held by the holding unit with respect to the base material.

According to another aspect of the present disclosure, a cell detaching method for detaching cells placed on a base material floating on an acoustic matching liquid, from the base material, the acoustic matching liquid being held by a holding unit includes detaching the cells from the base material by applying an ultrasonic vibration to the cells through the acoustic matching liquid and performing control to maintain a constant height of a fluid level of the acoustic matching liquid held by the holding unit with respect to the base material during application of the ultrasonic vibration.

Further features of the present disclosure will become apparent from the following description of exemplary embodiments with reference to the attached drawings.

BRIEF DESCRIPTION OF THE DRAWINGS

FIG. 30 is a flowchart illustrating an example of temperature control processing of the cell detaching apparatus according to exemplary embodiments of the present disclosure.

FIG. 31 is a flowchart illustrating an example of detaching time count processing of the cell detaching apparatus according to exemplary embodiments of the present disclosure.

DESCRIPTION OF THE EMBODIMENTS

Figure 1:
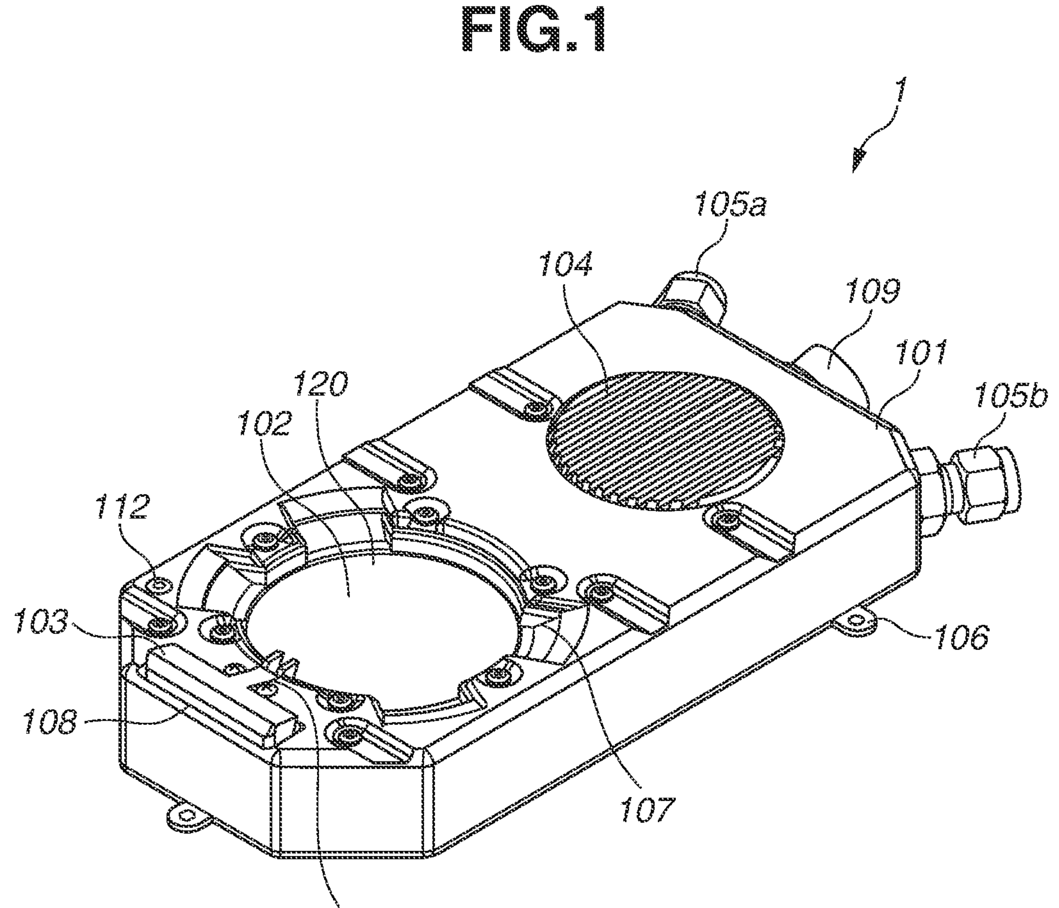
FIG. 1 illustrates a cell detaching apparatus according to a first exemplary embodiment of the present disclosure.

Although the cell detaching apparatus according to exemplary embodiments of the present disclosure will be describe below, the present disclosure is not limited to these exemplary embodiments. Cells to be detached may be in a state where each individual cell is wandering, a state where a plurality of cells is bonded, or a state where cells form a sheet (cell sheet).

(Cell Detaching Apparatus)

The cell detaching apparatus according to the present exemplary embodiment is an apparatus for detaching cells placed on a base material floating on an acoustic matching liquid, from the base material. The cell detaching apparatus includes a holding unit for holding the acoustic matching liquid, and a detaching unit for applying an ultrasonic vibration to the cells via the acoustic matching liquid to detach the cells from the base material. The cell detaching apparatus further includes a control unit for maintaining a constant height of the fluid level of the acoustic matching liquid held by the holding unit, with respect to the base material, during application of the ultrasonic vibration. The above-descried configuration enables reducing variation of the vibration transmitted to the cells during application of the ultrasonic vibration.

A cell culture apparatus discussed in Japanese Patent Application Laid-Open No. 2019-170305 operates a cooling mechanism and a vibration mechanism based on a result of determining whether to operate the cooling mechanism and the vibration mechanism based on a cell image. However, there has been an issue of the cell freshness degradation at low temperatures, and only cooling is insufficient to solve the issue. There has been no method for knowing the cell temperature. Although a method for acquiring a cell image for knowing the timing to start the cell detaching is described, it is difficult to suitably determine to start the cell detaching since the cell image may include an illumination unit reflected on the curved wall surface of the edge portion of a culture vessel.

Maintaining a constant contact area between the acoustic matching liquid and the holding unit and a constant amount of the acoustic matching liquid enables reducing variation of the vibration transmitted to the cells during application of the ultrasonic vibration.

Control for maintaining a constant height of the fluid level means maintaining the height of the fluid level within ±2.0 mm from the fluid level at the timing when the application of the ultrasonic vibration is started. It is more preferable to maintain the fluid level within ±1.5 mm.

Examples of the above-described acoustic matching liquid include water and gel-formed materials.

Cells placed on the base material may be directly bonded to the base material. Alternatively, the base material, temperature-responsive polymer, and cells may be disposed in this order. In the latter case, cells are detached not only from the base material but also from the temperature-responsive polymer.

The acoustic matching liquid may be referred to as a vibration transmission substance, and the holding unit as a vibration tub.

(Descriptions of Issues)

The conventional cell detaching apparatus has an issue that a dish needs to be stably vibrated.

A vibration transmission substance exists between the vibrator and the dish. Since the amount of the vibration transmission substance therebetween is not constant, the detaching condition changes each time. This is because the control of the fluid volume has been devised.

Further, the inconstant amount of a vibration transmission fluid causes temperature variation, largely affecting the cell detaching. There has been an issue that an optimal temperature range is required for the cell survival, and temperature variations adversely affect or degrade the cell quality (survival rate and detaching rate).

In particular, the combined use of the temperature-responsive polymer remarkably affects the cell quality. Generally, the temperature around 37° C. is said to be preferable for cells. The cell detaching requires that the temperature be lowered to and maintained at around 20° C. This requires temperature control (heating and cooling control) since the temperature of cells including the culture medium is varied by the heat generated by the driving power of the vibrator. A heater and a cooler are disposed around the dish to heat and cool the cells. There is an issue that temperature irregularities occur since heat conduction is made from a local portion to control the dish temperature.

(Descriptions of Cell Detaching Apparatus)

To solve the above-described issue, the following method for maintaining an optional water volume (fluid volume) has been devised. In the method for solving the issue, a tub for optionally storing the vibration transmission fluid (vibration tub) is provided, which has not been used in the conventional method, to allow the vibration transmission fluid to overflow upon placement of the dish.

Constantly maintaining a constant water volume in this way enables stabilizing the transmitted vibration to suitably maintain the detaching force applied to the cells, thus stabilizing the quality of the cells to be collected. A storage tub for collecting the overflowing vibration transmission fluid is further provided next to the vibration tub to implement a structure for temporarily storing the fluid. Putting a sinking weight into and taking it out of the storage tub enable returning the overflowing vibration transmission fluid to the vibration tub in addition to removing the dish after completion of the cell detaching. Repeating this sequence enables performing the cell detaching procedures while supplying the fluid to cover the reduced amount.

In this case, providing fluid level indicators (indicator line and form) on either one or both of the storage tub and the vibration tub makes it easier to control the required fluid volume. The indicators indicate the upper limit (when the fluid is replenished) and the lower limit (when the fluid is reduced) of the required fluid volume. The inventors have devised a simpler method for solving this issue, which will be described below. When the dish is put in the vibration tub, a weight is placed because buoyancy acts. The newly devised structure moves the sinking weight in association with the operation for placing the weight and the operation for removing the weight, without using power or sensing.

The vibration transmission fluid moves through a fluid path disposed between the vibration tub and the storage tub. A mountain-like projection with an optional height is disposed on the bottom surface of the fluid path. This projection increases the wetting angle to make it easier to drain off the fluid on the fluid path, further stabilizing the fluid volume.

Instead of using the above-described gravity-based sinking weight, the fluid path may be provided with a cover (plug). For example, a similar effect can also be obtained by using a float on the vibration tub side to plug the water path at the float position.

Further, providing the storage tub and the vibration tub enables controlling the water temperature. Disposing a water tube at a position around either one or both of the vibration tub and the storage tub enables directly supercooling the vibration transmission fluid. This also enables the combined use of a detaching method based on temperature-responsive polymer or enzyme. When heating or cooling the cells as a detaching method, it is necessary to transmit heat to the vibration tub. However, disposing a heat conductive plate to the vibrator inevitably causes temperature irregularities along the heat conduction path in the vibration tub. Floating the dish and generating a rectilinear current by using an ultrasonic vibration disperses the vibration transmission fluid in the vibration tub, resulting in a uniform fluid. This enables directly adjusting the temperature of the vibration transmission fluid from the bottom surface of the vibrator.

As a similar method, the vibration transmission fluid may be circulated by using the water path. In this case, the vibration transmission fluid is stored in a separately prepared storage tub such as a tank. The vibration transmission fluid can be heated or cooled when passing through the storage tank, providing a temperature controller enables controlling the temperature of the vibration tub, and temperature control most suitable for the cell culture can further be performed.

The present exemplary embodiment includes a vibration vessel where a floating vessel containing the cells can be optionally placed, and maintains a constant amount of the vibration transmission fluid. The vibration transmission fluid adheres to the outside of the dish bottom to decrease in amount in each operation. Therefore, to enable supplying the required amount of the vibration transmission fluid each time, the present exemplary embodiment includes a storage tub for storing the vibration transmission fluid of such an amount that covers the reduced amount.

Descriptions of Effects

The conventional method cannot stably vibrate the dish with a suitable amount of the vibration transmission fluid. With the conventional apparatus, although the vibration transmission substance exists between the ultrasonic transducer and the dish, there is no structure for storing the vibration transmission substance between the dish and the vibrator. Therefore, the amount of the vibration transmission fluid cannot be maintained constant. Thus, fluid volume control is required since the condition for transmitting a suitable energy changes each time. In addition, an unstable fluid volume affects the temperature radiation and the vibration transmission, making temperature control difficult.

The storage tub is provided because such a structure enables optionally placing the dish (vessel), facilitating the cell detaching procedures. Further, the structure that includes the vibration tub for vibrating the dish in the fluid enables uniformly irradiating the cells with a constant amount of the vibration transmission fluid, and also includes the fluid path for connecting the vibration tub and the storage tub.

Since the required fluid level position is determined by the height of the bottom of the fluid path, the amount of the vibration transmission fluid can be uniformly maintained constant. A newly devised method for optionally setting the fluid level position of the storage tub enables stabilizing the vibration energy transmitted to the dish. This makes it possible to stably maintain the required amount of energy to be applied to the cells, thus providing high-quality cells. Further, the present exemplary embodiment provides a low-cost, energy-saving, and ecological cell detaching apparatus that requires no pump and drains off no waste of the vibration transmission fluid.

According to the present exemplary embodiment, a tub for optionally storing the vibration transmission fluid (vibration tub) is provided, which has not been used in the conventional method, to allow the vibration transmission fluid to overflow upon placement of the dish, making it possible to maintain an optional water volume. This enables stabilizing the amount of energy in the cell detaching to provide high-quality cells.

A storage tub for collecting the overflowing vibration transmission fluid is further provided next to the vibration tub to implement a structure for temporarily storing the fluid. Putting a sinking weight into and taking it out of the storage tub enable returning the overflowing vibration transmission fluid to the vibration tub in addition to removing the dish after completion of the cell detaching. Repeating this sequence enables performing the cell detaching procedures while supplying the fluid to cover the reduced amount. This makes it easier to collect and reuse the vibration transmission fluid. This enables stabilizing the amount of energy in the cell detaching to provide high-quality cells and also provides an ecological low-price cell detaching apparatus.

In this case, providing fluid level indicators (indicator line and form) on either one or both of the storage tub and the vibration tub makes it easier to control the required fluid volume. The indicators indicate the upper limit (when the fluid is replenished) or the lower limit (when the fluid is reduced) of the required fluid volume. This enables stabilizing the amount of energy in the cell detaching to provide high-quality cells and at the same time provides an ecological, low-price, and easy-to-handle cell detaching apparatus.

When the dish is placed in the vibration tub, buoyancy acts on the dish and hence a weight is placed on the dish so that the dish comes into contact with a vibration plate. The newly devised structure moves the sinking weight in association with the operation for placing the weight and the operation for removing the weight, without using power or sensing. This enables stabilizing the amount of energy in the cell detaching to provide high-quality cells and at the same time provides an ecological, low-price, and easy-to-handle cell detaching apparatus.

The fluid path disposed between the vibration tub and the storage tub is used to move the vibration transmission fluid. When the vibration transmission fluid passes through the fluid path, it passes along the mountain-like projection with an optional height disposed on the bottom surface of the fluid path. When the fluid reaches an optional fluid volume, the last fluid is divided by the mountain-like projection at a certain moment. At this timing, the wetting angle increases to make it easier to drain off the water on the water path, further stabilizing the water volume. This enables stabilizing the amount of energy in the cell detaching to provide high-quality cells and at the same time provides an ecological, low-price, and easy-to-handle cell detaching apparatus.

Instead of using the above-described gravity-based sinking weight, the water path may be provided with a cover (plug). For example, a similar effect can also be obtained by using a float on the vibration tub side to plug the water path at the float position.

Further, providing the storage tub and the vibration tub enables controlling the water temperature.

Disposing a water tube at a position around either one or both of the vibration tub and the storage tub enables directly supercooling the vibration transmission fluid. This also enables the combined use of a detaching method based on temperature-responsive polymer or detaching enzyme. When heating or cooling the cells as a detaching method, it is necessary to transmit heat to the vibration tub. However, disposing a heat conductive plate to the vibrator inevitably causes temperature irregularities along the heat conduction path in the vibration tub. Floating the dish and generating a rectilinear current by using an ultrasonic vibration disperses the vibration transmission fluid in the vibration tub, resulting in a uniform fluid. This enables direct temperature adjustment for the vibration transmission fluid from the bottom surface of the vibrator. This configuration enables providing higher quality cells because of not only stabilizing the amount of energy in the cell detaching but also improved variation of the detaching condition on temperature effects. In addition, this configuration enables providing an ecological, low-price, easy-to-handle, and small-sized cell detaching apparatus.

As a similar method, the vibration transmission fluid may be circulated by using the fluid path. In this case, the vibration transmission fluid is stored in a separately prepared storage tub such as a tank. The vibration transmission fluid can be heated or cooled when passing through the storage tank, providing a temperature controller enables controlling the temperature of the vibration tub, and temperature control most suitable for the cell culture can further be performed. This configuration enables providing higher quality cells because of not only stabilizing the amount of energy in the cell detaching but also improved variation of the detaching condition on temperature effects. In addition, this configuration enables providing an ecological, low-price, and easy-to-handle cell detaching apparatus.

The cell detaching apparatus according to the present exemplary embodiment includes a drain form for collecting and draining off the acoustic matching liquid. When the operator ends operating the cell detaching apparatus according to the present exemplary embodiment and drains off the acoustic matching liquid, the operator can conveniently discard the acoustic matching liquid without soiling the apparatus, thus acquiring effects of improved workability and maintainability. A storage stand provides an effect of retaining the drainage posture and conveniently performing operations without requiring a storage space at the time of drying.

The cell detaching apparatus according to the present exemplary embodiment includes a storage tub, a sinking weight vertically movable in the storage tub, and a rotatably separated lever, as a control unit for maintaining a constant height of the fluid level. This configuration enables downsizing the cell detaching apparatus. The separated lever makes it easier to clean the weight, providing an effect of improved maintainability.

The sinking weight has an arc shape and is provided with a through-hole rotatably contacting the lever at the central portion, providing an improved drainage performance of the acoustic matching liquid and improved maintainability. The arc shape of the sinking weight reduces the diameter of the cell detaching apparatus, providing an effect of apparatus downsizing.

A cell detaching unit according to the present exemplary embodiment includes a movable weir lever selectively and fixably rotating in contact to change the water level of the cell detaching apparatus. This configuration enables adjusting the height of the acoustic matching liquid to a required position to improve the detaching accuracy, and is effective for cell quality improvement.

The cell detaching apparatus according to the present exemplary embodiment is provided with step-like projecting portions for microscopic observation at the outer edge portion. The cell detaching apparatus is further provided with projecting portions at the height where the bottom surface of the holding unit substantially coincides with on-step projecting portions. This configuration enables the apparatus to fit into a microscopic stage table, providing an effect of reducing the distance between the object lens and the observation surface to allow selection of a high-magnification object lens.

The cell detaching apparatus according to the present exemplary embodiment includes a vibrator supporting member on the outer side of the average diameter of the ring-like piezoelectric element as the neutral axis of the cross-sectional shape. This configuration is effective in thinning the apparatus.

The cell detaching apparatus according to the present exemplary embodiment includes a temperature sensor in the vibration tub to monitor the internal temperature of the cell detaching apparatus. This configuration is effective for accurate temperature control and provides an effect of improved cell quality.

The cell detaching apparatus according to the present exemplary embodiment includes a heating unit for temperature control on the surface of the holding unit. This configuration is effective for accurate temperature control for the cell detaching apparatus and provides an effect of improved cell quality. In addition, the heating unit in laminate sheet form provides an effect of apparatus downsizing.

The cell detaching apparatus according to the present exemplary embodiment includes a tapered form on the bottom surface of the holding unit for holding the acoustic matching liquid, and an elastic member made of rubber at the tip of the holding unit. This configuration is effective in thinning the apparatus.

The cell detaching apparatus according to the present exemplary embodiment includes discontinuous portions on the outer edge projecting portions. This configuration is effective for apparatus downsizing.

The cell culture apparatus according to the present exemplary embodiment includes a temperature sensor for monitoring one or more of the vibrator, the vibration transmission substance, the vessel (dish), and the culture medium (culture solution), as a unit for measuring the cell temperature. This configuration maintains the cell freshness and improves the cell quality.

The cell culture apparatus according to the present exemplary embodiment includes a unit for controlling the vibration of the vibrator based on some pieces of sensor information. This configuration maintains the cell freshness and improves the cell quality.

The cell culture apparatus according to the present exemplary embodiment includes a unit for stopping the vibration when the temperature rises to a predetermined temperature. This configuration maintains the cell freshness and improves the cell quality.

The cell culture apparatus according to the present exemplary embodiment includes a unit for producing a vibration after the temperature drops to a predetermined temperature or below. This configuration maintains the cell freshness and improves the cell quality.

The cell culture apparatus according to the present exemplary embodiment includes a unit for controlling the cooling temperature based on sensor information. This configuration maintains the cell freshness and improves the cell quality.

The cell culture apparatus according to the present exemplary embodiment includes a unit for controlling a heating mechanism based on sensor information. This configuration maintains the cell freshness and improves the cell quality.

The cell culture apparatus according to the present exemplary embodiment includes a unit for bringing the vibration tub (holder) into close contact with the culture vessel. This configuration maintains the cell freshness and improves the cell quality.

The cell culture apparatus according to the present exemplary embodiment includes a unit for performing temperature control by using a water tube and a heat conductive metal in the vibration tub (holder). This configuration maintains the cell freshness and improves the cell quality.

The cell culture apparatus according to the present exemplary embodiment includes a housing having a bottom surface formed of a thin black material, and a space for enabling temperature variable control. This configuration maintains the cell freshness, improves the cell quality, and facilitates temperature control for the cell detaching apparatus.

The cell culture apparatus according to the present exemplary embodiment includes a piezoelectric element (dielectric material) formed of a heat conductive metal (a flexible copper foil is also applicable) and a thin insulation layer. This configuration maintains the cell freshness, improves the cell quality, and facilitates temperature control for the cell detaching apparatus.

The cell culture apparatus according to the present exemplary embodiment includes a cooling rod inside the vibrator to increase the cooling speed. This configuration maintains the cell freshness, improves the cell quality, and facilitates temperature control for the cell detaching apparatus.

The cell culture apparatus according to the present exemplary embodiment includes at least one concavo-convex shape on the vibrator of the vibrating member on the vibration tub side so that the vibration transmission substance (vibration transmission fluid) reaches the concavo-convex shape to increase the cooling speed. This configuration maintains the cell freshness, improves the cell quality, and facilitates temperature control for the cell detaching apparatus.

The cell culture apparatus according to the present exemplary embodiment includes an observation unit formed of an image sensor disposed at the top or bottom of the vessel of which the inside is illuminated by illumination light of a light emitting diode (LED), and the observation unit observes cells or a cell sheet in the vessel. This configuration improves the cell quality and facilitates temperature control for the cell detaching apparatus.

The cell culture apparatus according to the present exemplary embodiment includes a unit for generating a warning sound and displaying a warning on a monitor. This configuration maintains the cell freshness, improves the cell quality, and facilitates temperature control for the cell detaching apparatus.

The cell culture apparatus according to the present exemplary embodiment includes a light emitting element with the optical axis inclined from the upper surface of the vibration plate to the piezoelectric element side. This configuration makes it easier to determine the cell detaching and facilitates temperature control for the cell detaching apparatus, thus improving the cell quality.

(Example Configuration of Cell Detaching Apparatus)

The cell detaching apparatus according to the present exemplary embodiment may include a vibration tub for holding an acoustic transmission medium, and a storage tub for storing the acoustic transmission medium in addition to the vibration tub. The acoustic transmission medium is flowably connected with the storage tub via a fluid path, and the storage tub includes a sinking member to enable controlling the water level of the vibration transmission fluid.

The cell detaching apparatus according to the present exemplary embodiment may be configured so that the leading end of the sinking member moves down in the storage tub across the rotation center by the self-weight. The sinking member may be attachable to and detachable from the storage tub. The sinking member may be stored in the fluid path, and a groove for flowing the acoustic transmission medium may be provided on the side opposite to the weight side across the rotation center. The fluid path may be provided with a mountain-like edge line. At least either one of the storage tub and the vibration tub may be provided with an indicator for indicating the fluid volume.

In addition, the vibration tub may be provided with a temperature sensor, and a water tube may be disposed around the vibration tub. The cell detaching apparatus may include a circulating pump and a temperature control tank for constant temperature control, and may be provided with a cooling fin to enable radiating heat larger than the heat quantity generated by the driving power.

The cell detaching apparatus according to the present exemplary embodiment includes a housing that may be provided with an observation window including a transparent member at the bottom portion of the housing. A light emitting element may be disposed inside the vibration tub or inside the housing.

The light emitting elements may be disposed at a plurality of positions on the vibration tub, facing each other in at least either one of tapered and stepped forms.

(Cell Detaching Method)

A cell detaching method according to the present exemplary embodiment is a method for detaching the cells placed on the base material floating on the acoustic matching liquid, from the base material. The cell detaching method includes at least the following processes:

(1) A detaching process for detaching the cells from the base material by applying an ultrasonic vibration to the cells through the acoustic matching liquid (2) A control process for maintaining a constant height of the fluid level of the acoustic matching liquid held by the holding unit, with respect to the base material, during application of the ultrasonic vibration.

EXEMPLARY EMBODIMENTS

Exemplary embodiments of the present disclosure will be described below. However, the present disclosure is not limited thereto.

The cell detaching apparatus according to a first exemplary embodiment of the present disclosure will be described below with reference to FIGS. 1, 2, 4, and 16.

Figure 2:
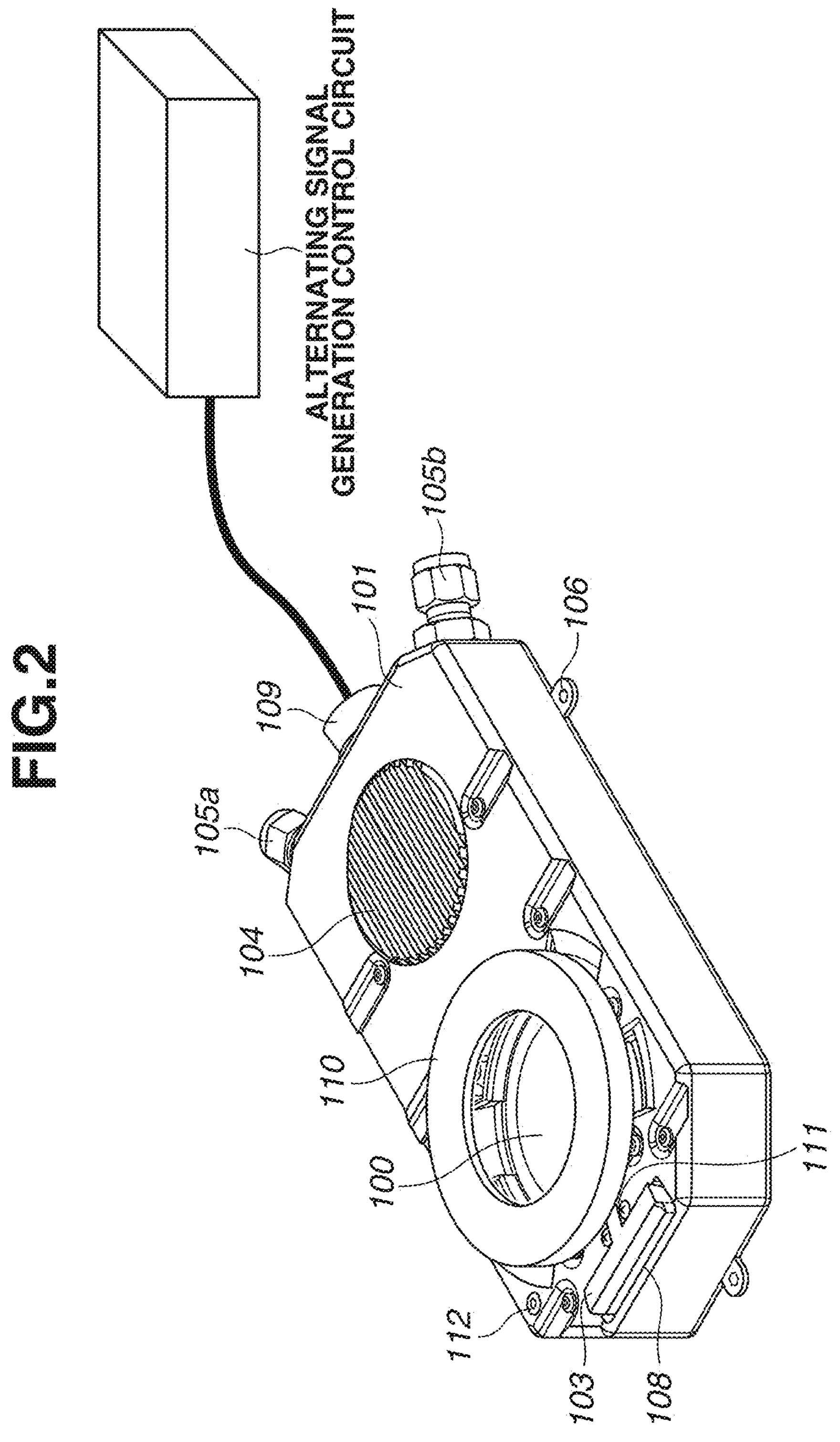
FIG. 2 illustrates an operating condition of the cell detaching apparatus with a culture vessel placed according to the first exemplary embodiment of the present disclosure.

FIG. 2 illustrates a cell culture vessel 100 and a state where a dish weight 110 is placed to prevent the culture vessel 100 from floating on the vibration transmission fluid (not illustrated in FIG. 2). This apparatus vibrates when an alternating signal is applied to a piezoelectric element 117 of a vibration plate 102. FIG. 2 illustrates a case where the alternating signal is applied from an alternating signal generation control circuit outside the apparatus. This circuit may be built in a housing 101.

The cell detaching apparatus will be described below with reference to FIG. 1. The housing 101 includes a vibration tub 107 filled with a vibration transmission fluid (not illustrated) such as water or glycerin. The vibration plate 102 bonded with the piezoelectric element 117 for producing an ultrasonic vibration is disposed on the bottom member of the vibration tub 107, being sealed by a rubber packing 120. A storage tub 108 is disposed next to the vibration tub 107 in a groove form so that the vibration transmission fluid is freely movable between the two tubs through a fluid path 111.

Figure 16:
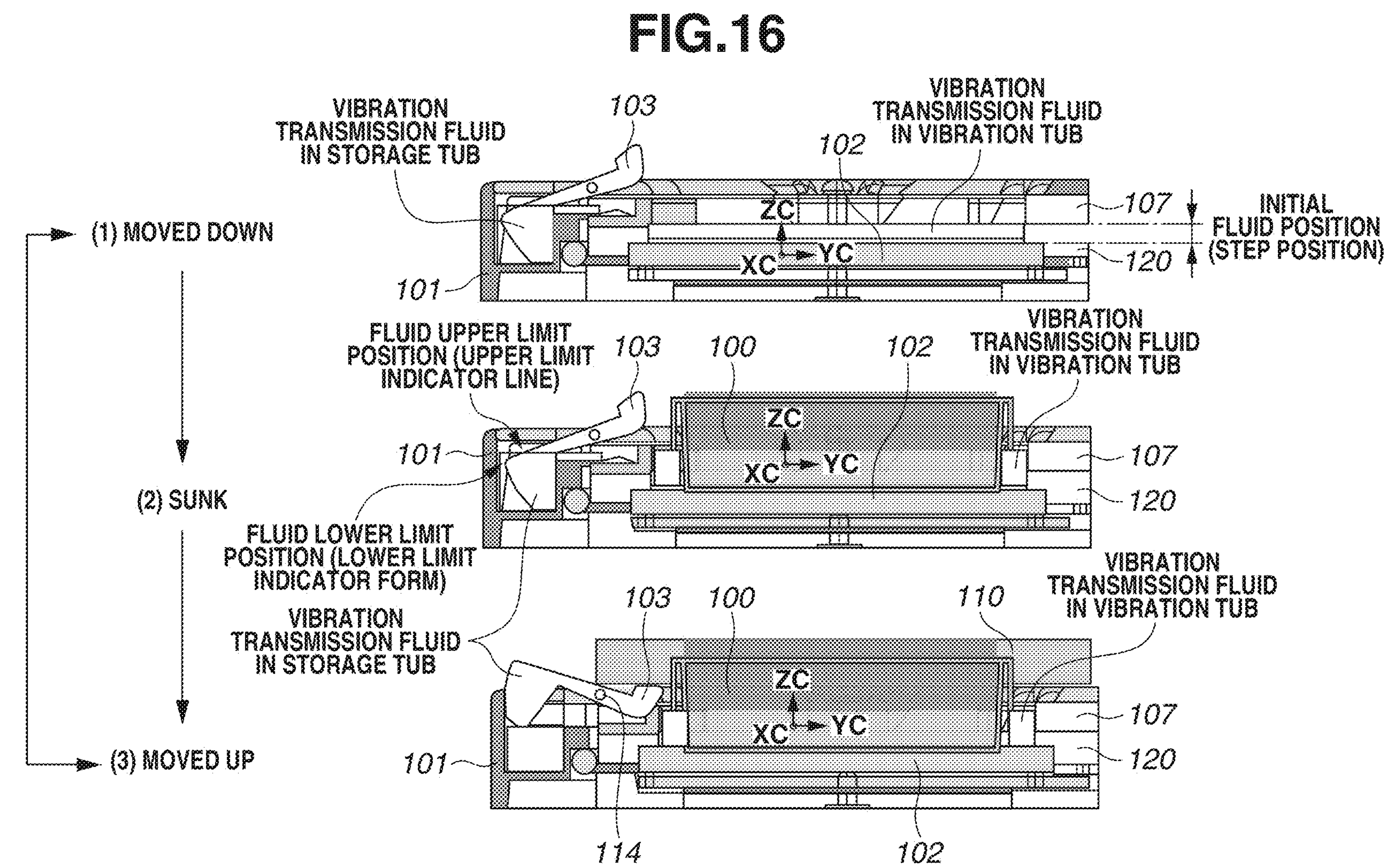
FIG. 16 illustrates an example configuration of a water level control processing of the cell detaching apparatus according to exemplary embodiments of the present disclosure.

A sinking weight 103 is provided to allow the vibration transmission fluid to move from the vibration tub 107 to the storage tub 108 and vice versa through the fluid path 111. FIG. 16 illustrates a transition of the moving state of the vibration transmission fluid. The weight portion of the sinking weight 103 moves up and down. When the sinking weight 103 moves up, the vibration transmission fluid moves from the vibration tub 107 to the storage tub 108. When the sinking weight 103 moves down, the vibration transmission fluid moves from the storage tub 108 to the vibration tub 107. When the culture vessel 100 is placed in the apparatus of the present exemplary embodiment in a state where the weight is downed (state <1>), the apparatus enters state <2>. In state <2>, the vibration transmission fluid overflows into the fluid path 111 by the volume of the immersion of the culture vessel 100, and both the storage tub 108 and the vibration tub 107 are filled with the vibration transmission fluid. When the dish weight 110 flops over the sinking weight 103 to raise the sinking weight 103 by weight, the vibration transmission fluid flows out to the side of the storage tub 108. At this timing, the vibration transmission fluid overflowing by the sinking weight 103 raised by the dish weight 110 passes through the fluid path 111 and flows into the storage tub 108 until the fluid level reaches the bottom height of the groove as the fluid path 111. The fluid level (not illustrated) is kept constant at the bottom height of the groove. The cell detaching apparatus is configured so that, when the dish weight 110 and the culture vessel 100 are taken out, the sinking weight 103 moves down, and the vibration transmission fluid in the storage tub 108 is returned to the vibration tub 107.

When a cell detaching apparatus 1 according to the present exemplary embodiment is used at a different place, there is a risk that the apparatus is inclined. Therefore, a level 112 is provided to check whether the place is inclined or adjust the inclination each time the apparatus is placed. This enables high-accuracy water level control.

The cell detaching apparatus is configured to be sealed by an O-ring 121 to prevent water entry from the bottom surface of the housing 101 in case of an extreme level collapse or cleaning. Since the bottom surface of the housing 101 is in contact with a workbench and subjected to a fluid spill, the bottom surface is coated with an antibacterial agent to prevent the multiplication of various germs.

Preparing an optional platform 125 makes it easier to make level. Recessed portions 126 for dish are engraved on the platform 125 to enable the dishes 100 to be aligned. Arranging recessed portions 127 for water absorbent paper enables absorbing spilled fluid. To adjust level, positioning members 129 are provided at three different positions so that the cell detaching apparatus 1 can be placed at a specific position. This enables constantly stabilizing the fluid position of the cell detaching apparatus 1. In addition, the front part of the platform 125 is raised (right back side in FIG. 17) by rubber bases 130 attached to the four corners. This enables level adjustment for the cell detaching apparatus 1 only with adjustment screws 128*a* and 128*b* at two different positions.

A second exemplary embodiment of the present disclosure will be described below with reference to FIG. 3.

Figure 3:
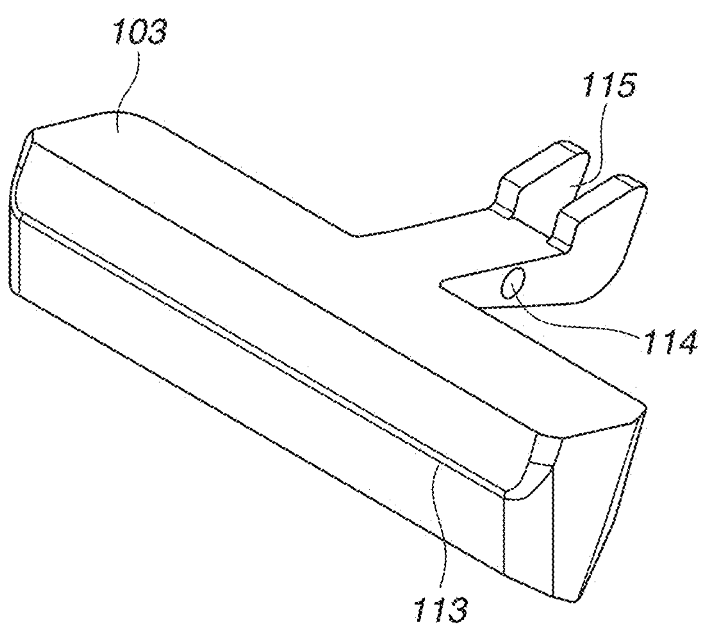
FIG. 3 illustrates a sinking weight according to second and third exemplary embodiments.

FIG. 3 illustrates in detail the sinking weight 103 described above with referenced to FIG. 1.

The sinking weight 103 is configured such that one piece is made larger than the other across the rotation center 114. The leading end of the sinking weight 103 moves down by the self-weight. As a matter of course, the larger the weight ratio of the larger piece to the smaller piece, the more the sinking weight 103 can be downsized. The sinking weight 103 is made of a material having a larger specific gravity than the vibration transmission fluid. For example, aluminum or brass having a larger specific gravity than water having a specific gravity of 1 is used. Depending on a selected processing (molding) method, resins having a specific gravity larger than 1, such as a polyacetal resin, are applicable. However, the sinking weight 103 needs to be raised by the dish weight 110. The rotation center 114 is configured to be rotatable while being fitted to the rod shape. Further, the sinking weight 103 is formed to be attached to and detached from the housing 101 illustrated in FIG. 1.

For example, as illustrated in FIG. 1, the sinking weight 103 is formed to be easily removed by detaching the screws at two different positions and then cleaned.

A third exemplary embodiment of the present disclosure will be described below with reference to FIG. 3.

The sinking weight 103 is downsized since disposing the sinking weight 103 illustrated in FIG. 3 at a position for fitting to the fluid path 111 illustrated in FIG. 1 enables storing the mechanism in the fluid path 111. The sinking weight 103 is downsized taking into consideration a demand for thinning when the apparatus is used together with a microscope or other measuring instruments. Simply disposing the sinking weight 103 in the fluid path 111 degrades the flowability of the vibration transmission fluid, disabling water volume control. Therefore, according to the present exemplary embodiment, disposing a groove 115 on the side opposite to the weight side (larger piece) of the sinking weight 103 across the rotation center 114 secures the flowability of the vibration transmission fluid without disturbing the water path. This configuration enables further increasing the weight ratio of the larger piece to the smaller piece.

A fourth exemplary embodiment of the present disclosure will be described below with reference to FIG. 4.

Figure 4:
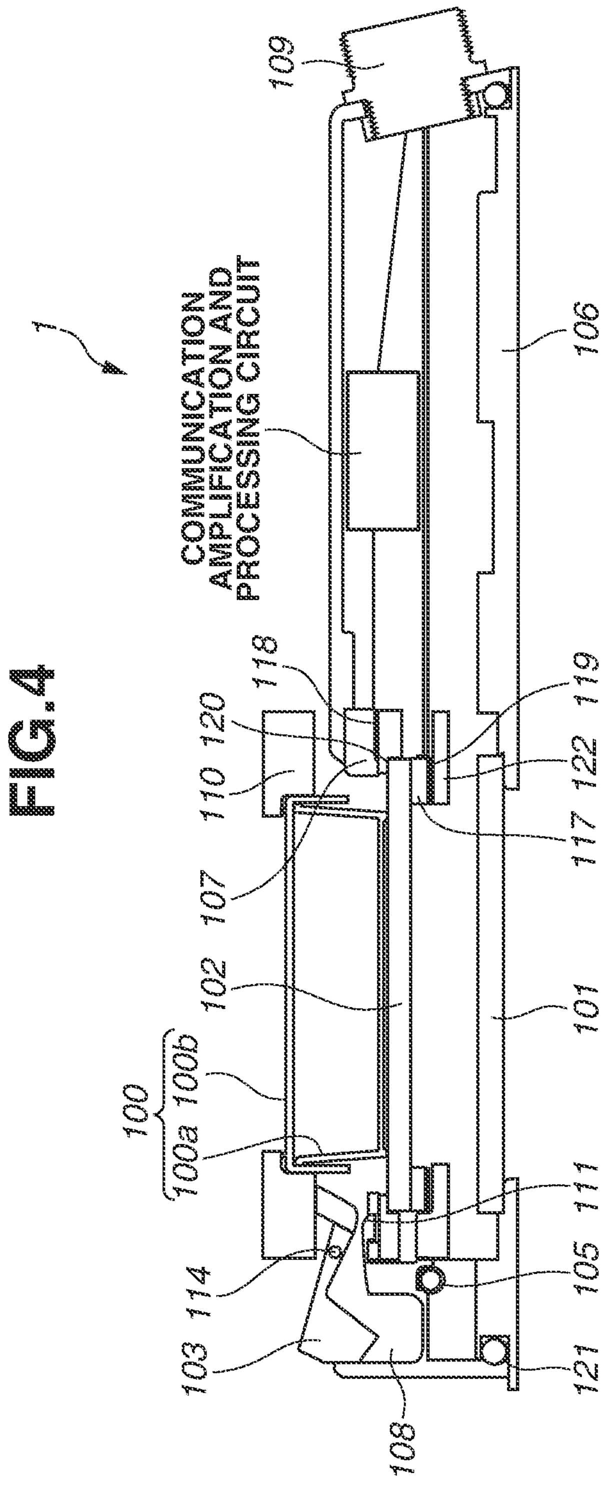
FIG. 4 is a cross-sectional view illustrating a cell detaching apparatus according to exemplary embodiments of the present disclosure.

FIG. 4 is a cross-sectional view illustrating the cell detaching apparatus 1 according to the fourth exemplary embodiment. The fluid path 111 is provided with a mountain-like edge line. This edge line is intended to stabilize the fluid level to secure a large wetting angle and improve the fluid flowability.

A fifth exemplary embodiment of the present disclosure will be described below with reference to FIGS. 5, 15, 14, 16, and 17.

Figure 5:
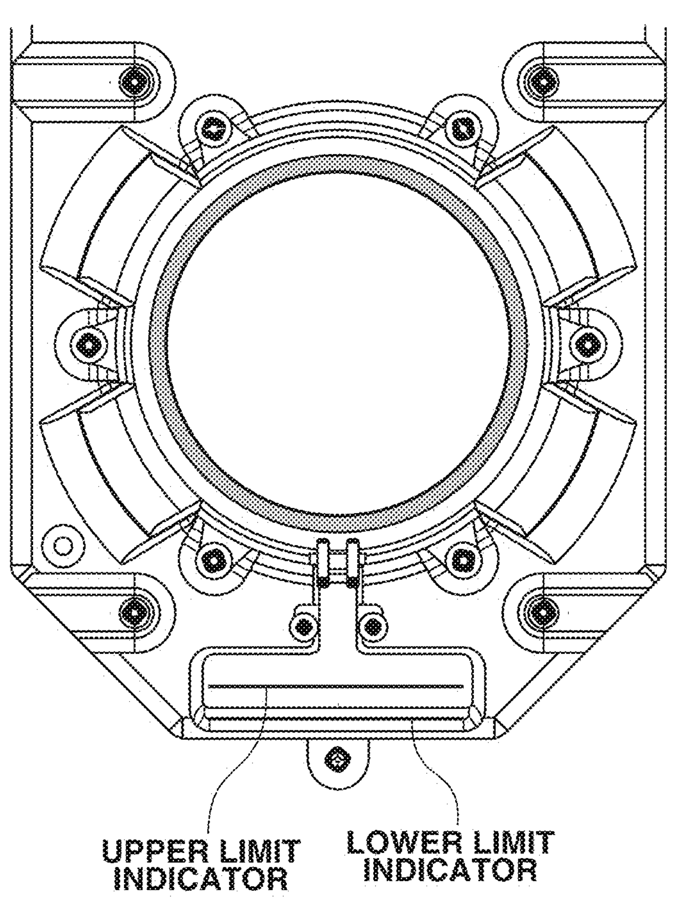
FIG. 5 illustrates an example configuration of fluid volume indicators of the cell detaching apparatus according to exemplary embodiments of the present disclosure.

Providing fluid level indicators (indication line and form) on either one or both of the storage tub 108 and the vibration tub 107 makes it easier to control the required fluid volume. Examples of indicators are illustrated in FIG. 5. The indicators indicate the upper limit (when the fluid is replenished) or the lower limit (when the fluid is reduced) of the required fluid volume, as illustrated in FIG. 5.

Figure 15:
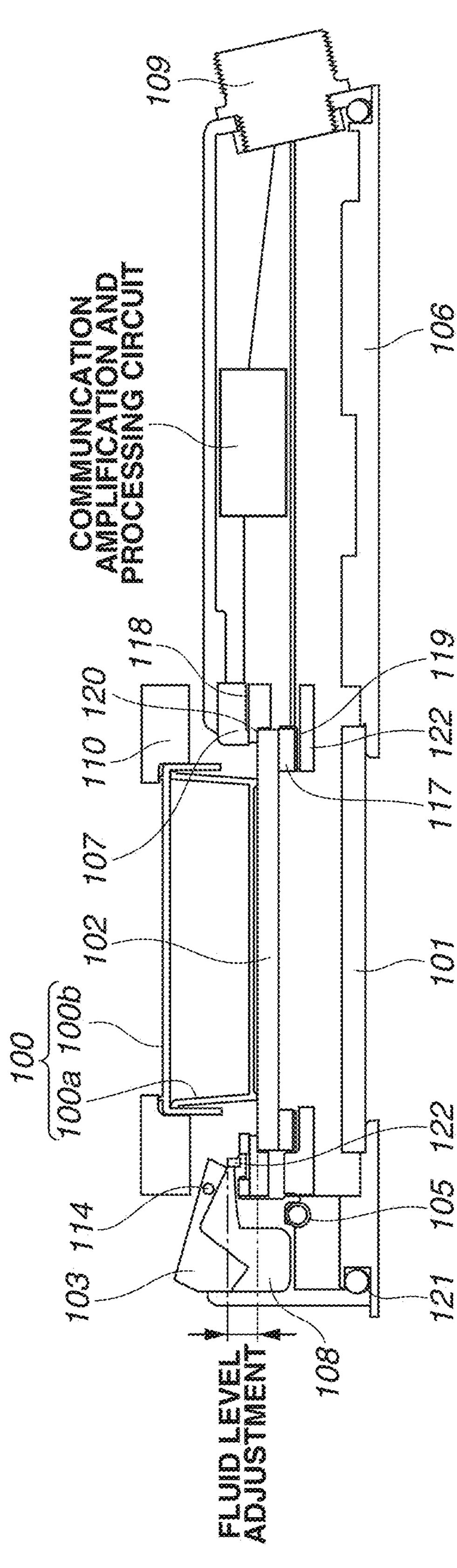
FIG. 15 illustrates an example configuration of a partition plate (water level adjustment plate) of the cell detaching apparatus according to exemplary embodiments of the present disclosure.

As illustrated in FIG. 15, either one or both of the storage tub 108 and the vibration tub 107 may be provided with a step form.

FIG. 16 illustrates the required fluid volume. In state <1>, the position of the step provided in the vibration tub 107 is the initial fluid position, and the fluid is injected from the storage tub 108. State <2> represents the fluid volume in a state where the dish 100 is immersed and abutted to the bottom of the vibration plate 102. It is possible to immediately visually recognize whether the fluid volume is within a suitable volume rage between the upper limit indicator line and the lower limit indicator form on the sinking weight 103. After the apparatus is repetitively operated, the fluid adheres to the dish 100. When the water volume falls below the lower limit indicator, the fluid is replenished up to the upper limit indicator, enabling constant fluid volume control.

Figure 17:
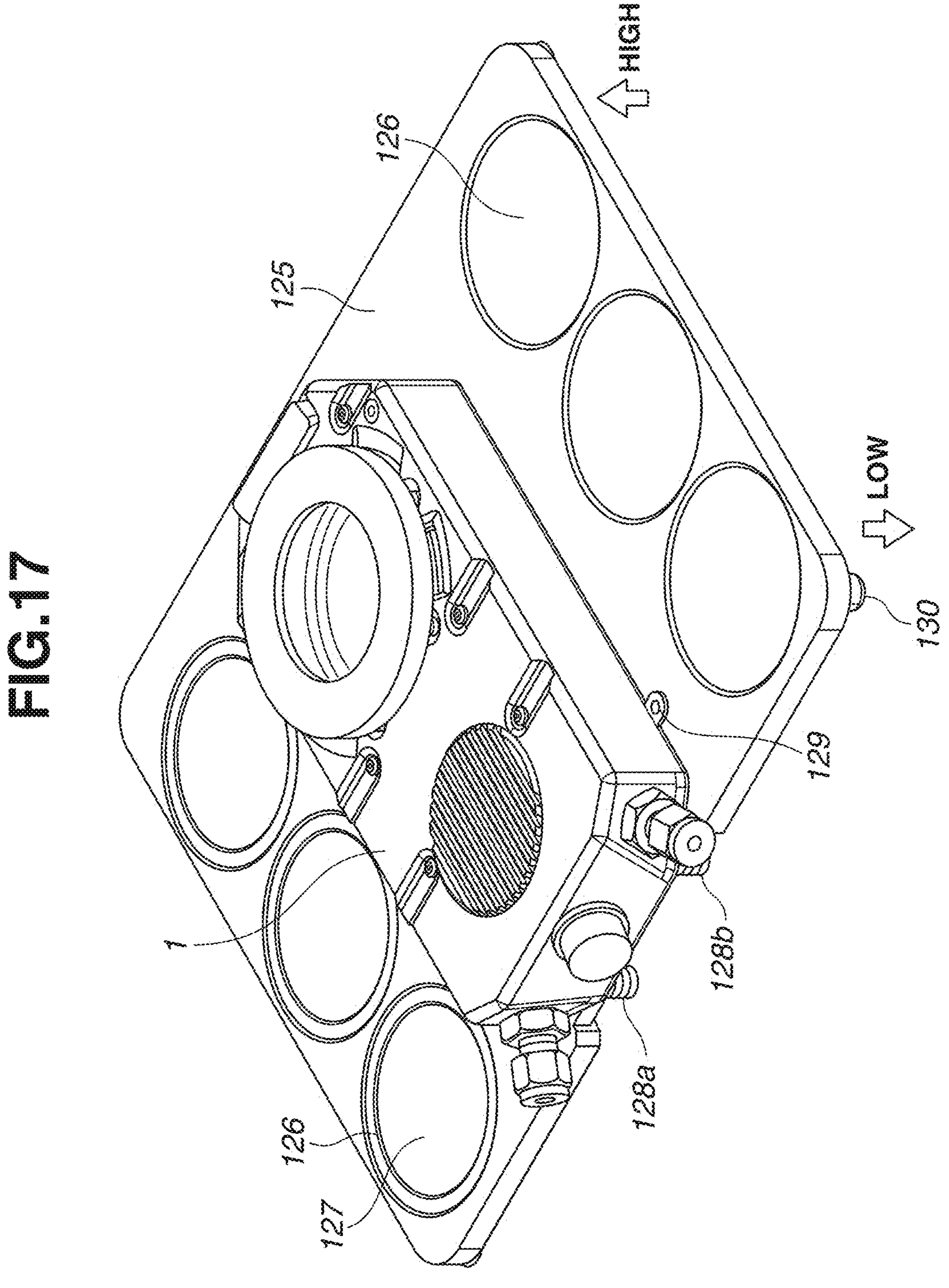
FIG. 17 illustrates an example configuration of a platform of the cell detaching apparatus according to exemplary embodiments of the present disclosure.

As illustrated in FIG. 17, a platform 125 for placing the dish 100 is disposed so that the fluid adhering to the dish 100 can be wiped off. The platform 125 is provided with the recessed portions 126 for dish in which the dishes 100 fit. The side for placing the dishes 100 after the cell detaching is provided with the recessed portions 127 for water absorbent paper so that water absorbent paper, filter paper, plain paper, or a cloth can be placed.

The use of the platform 125 also enables horizontal level adjustment.

Figure 6:
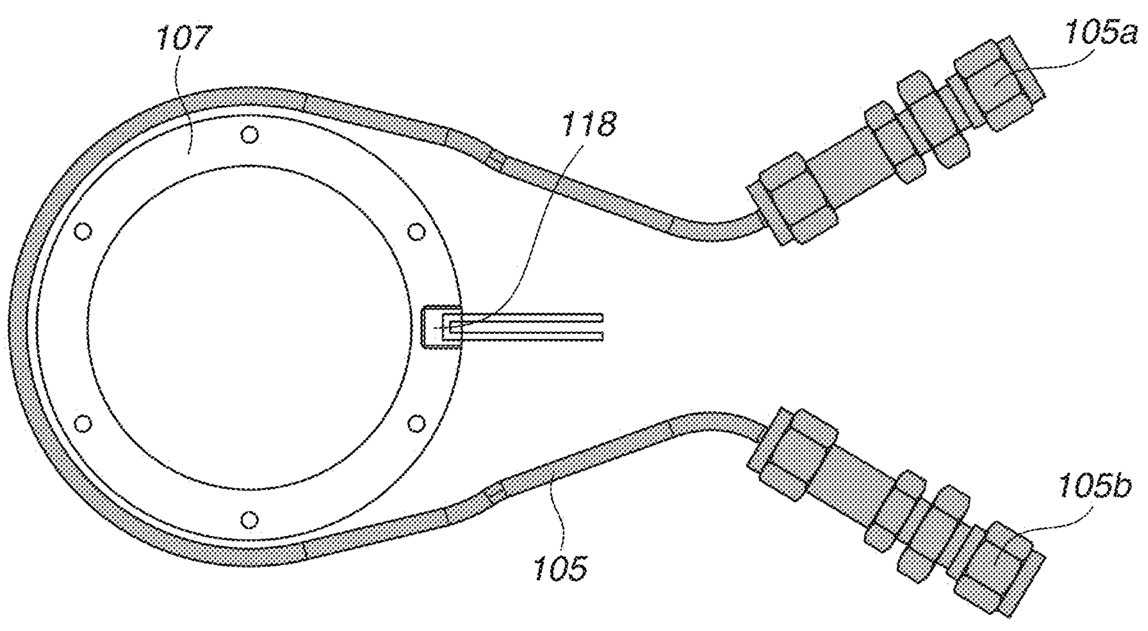
FIG. 6 illustrates an example configuration of the cell detaching apparatus using a fluid tube according to exemplary embodiments of the present disclosure.
Figure 7:
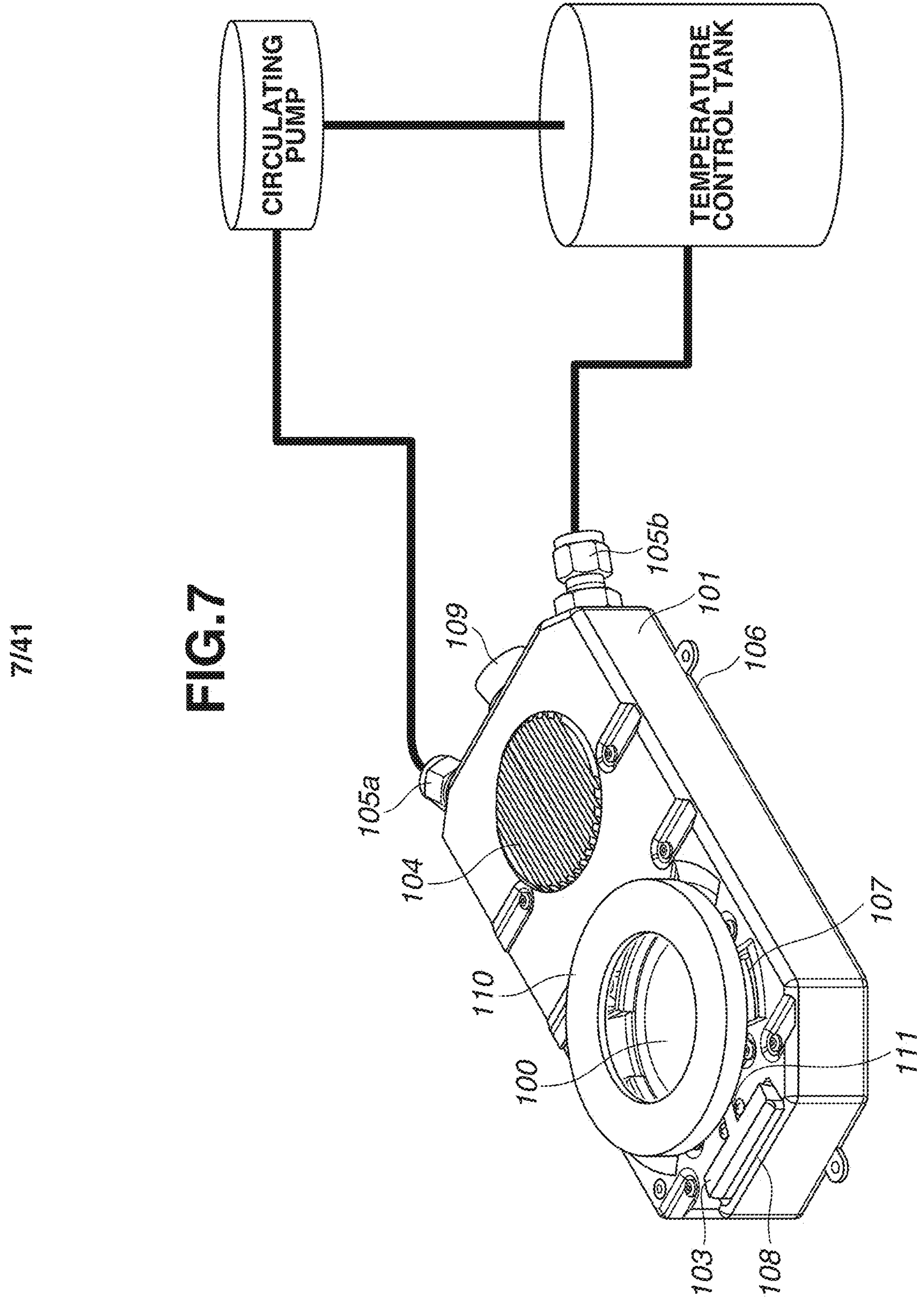
FIG. 7 illustrates an example configuration of the cell detaching apparatus with fluid circulation according to exemplary embodiments of the present disclosure.

A sixth exemplary embodiment of the present disclosure will be described below with reference to FIGS. 6 and 7.

Temperature variations largely affect the cell detaching. Therefore, a temperature sensor 118 is disposed in nip contact with the vibration tub 107. The temperature sensor 118 may be fixed with any fixing method such as bonding. This configuration enables direct or indirect temperature measurement for the culture surface (bottom surface) of the cell culture vessel 100. The temperature of the cells including the culture medium is varied by the heat generated by the driving power of the piezoelectric element 117 as a vibration source for the vibration plate 102. Therefore, a water tube 105 is disposed for cooling so as to surround the vibration tub 107 for the purpose of temperature control. Flowing hot water in the water tube 105 also allows the water tube 105 to be used for temperature control for the heating side. The temperature control unit is illustrated in detail in FIG. 7.

For example, the side of a water tube 105*a* is set as the inflow side of water (e.g., refrigerant), and the side of a water tube 105*b* is set as the outflow side of water. The temperature control unit includes the temperature control tank (FIG. 7) for subjecting the water in the vessel to constant temperature control to a specified temperature by using the circulating pump (FIG. 7) for circulating water. Generally, the temperature control unit is known as a cooling water circulation apparatus or a chiller. For the cell detaching apparatus, the water flow direction is not cared.

The housing 101 is provided with a cooling fin 104 to radiate heat equal to or larger than the heat quantity generated by the driving power of the piezoelectric element 117 as a vibration source for the vibration plate 102. However, for energy saving, the apparatus has a structure for avoiding the cooling operation as much as possible during normal operation.

Figure 12:
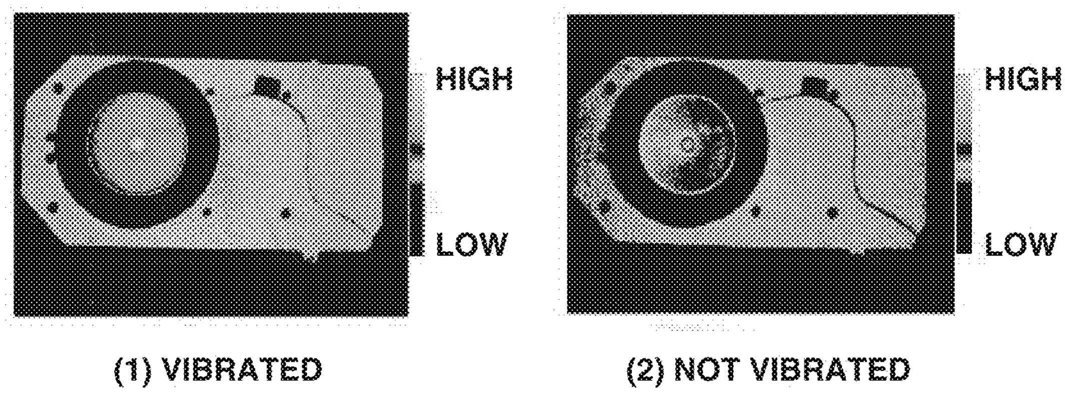
FIG. 12 illustrates surface temperature distributions of the cell detaching apparatus according to exemplary embodiments of the present disclosure.

The water tube 105 is disposed so as to surround the vibration tub 107 for the purpose of temperature control. However, according to the present exemplary embodiment, a plurality of the fluid paths 111 may directly circulate the vibration transmission fluid in the vibration tub 107, as illustrated in FIG. 12.

A seventh exemplary embodiment of the present disclosure will be described below with reference to FIG. 8.

In the cell detaching apparatus for detaching the cells from the bottom of the culture vessel according to the seventh exemplary embodiment, the operator may take out the dish 100 and visually check the detaching state of the bonded cells to confirm that the cells have been detached. According to the present exemplary embodiment, therefore, an observation window 116 made of a glass plate is provided on the bottom side of the housing 101 to observe the state of the bottom surface of the dish 100 with the cells bonded thereto, from the bottom side of the apparatus.

This enables observing the portion of the dish 100 with the cells bonded thereto.

Figure 8:
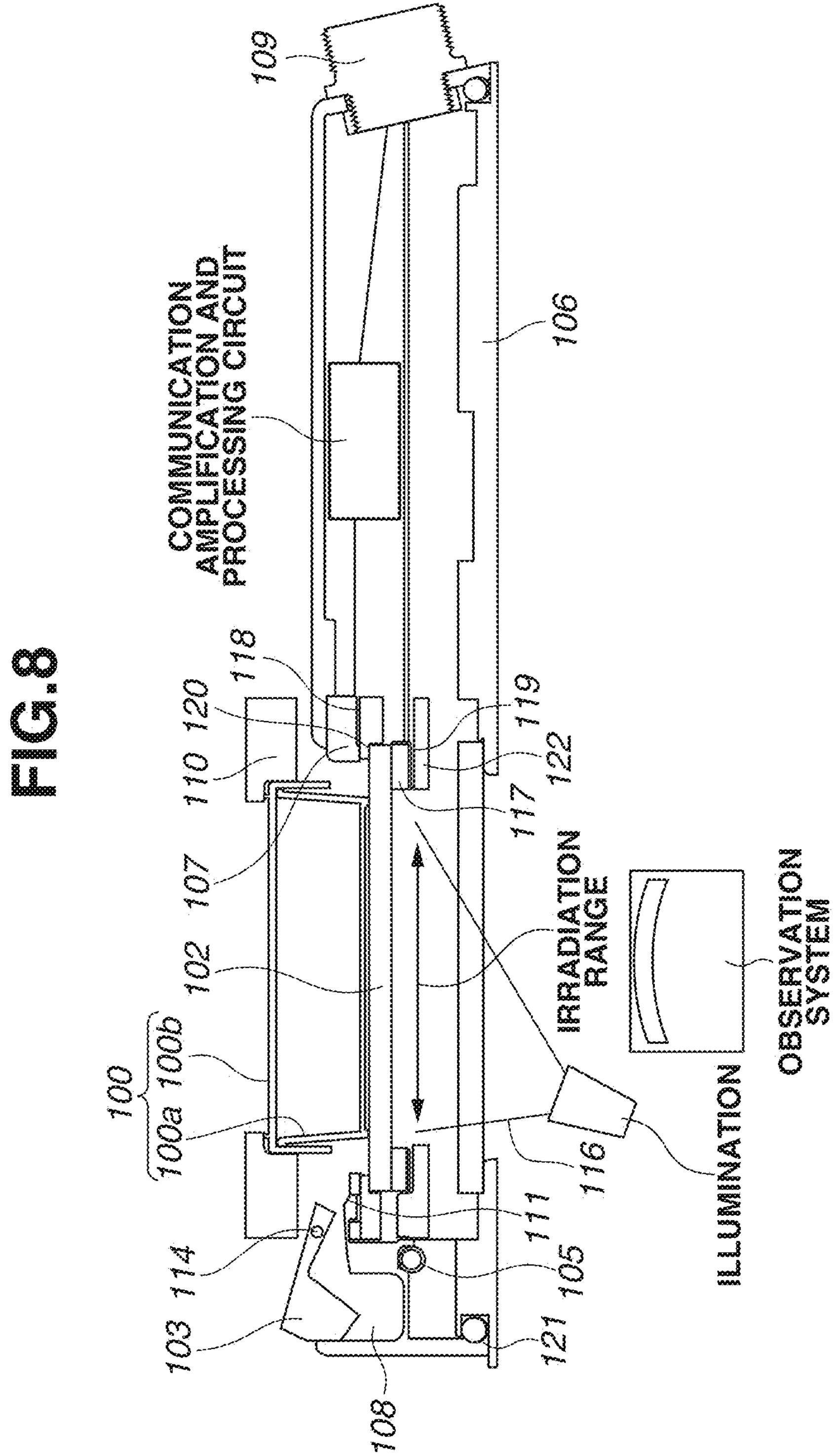
FIG. 8 illustrates an example configuration of the cell detaching apparatus including an observation system according to exemplary embodiments of the present disclosure.

An observation system is illustrated in FIG. 8. In this case, the vibration plate 102 of the vibration tub 107 is formed of a transparent glass plate and the piezoelectric element 117 adhesively bonded to the glass plate. When the transparent portion (irradiation range) of the vibration plate 102 is irradiated with illumination light, the cells in the dish 100 are illuminated through the transparent glass plate, facilitating the observation.

An eighth exemplary embodiment of the present disclosure will be described below with reference to FIGS. 9 and 10.

The eighth exemplary embodiment relates to the illumination unit according to the eighth exemplary embodiment.

Figure 9:
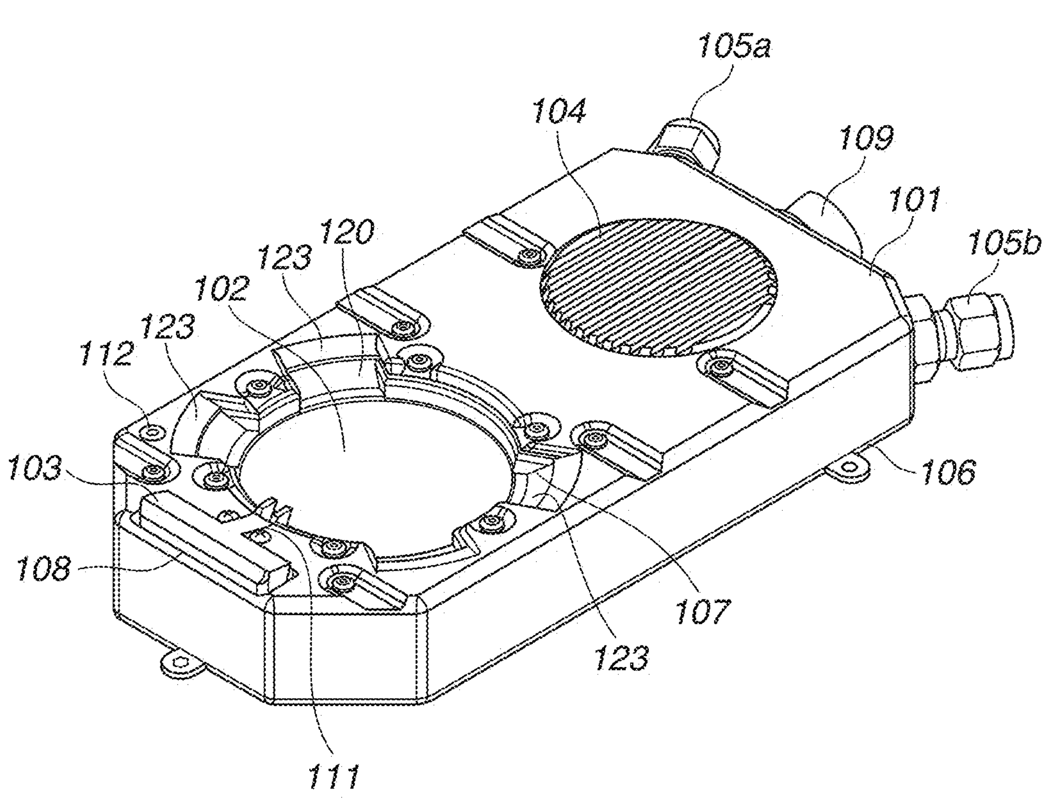
FIG. 9 illustrates an example configuration of the cell detaching apparatus including an illumination system according to exemplary embodiments of the present disclosure.

The vibration tub 107 in FIG. 9 is made of a transparent resin such as transparent polycarbonate or silicon rubber. The surface of the transparent resin member of the vibration tub 107 is made semi-transparent. The vibration tub 107 is configured such that LED lights 123 disposed inside the vibration tub 107 or the housing 101 indirectly irradiate the inside to scatter illumination to uniformly illuminate the dish 100. FIG. 10 illustrates specific arrangements of the LED lights 123 on the vibration tub 107.

Figure 10:
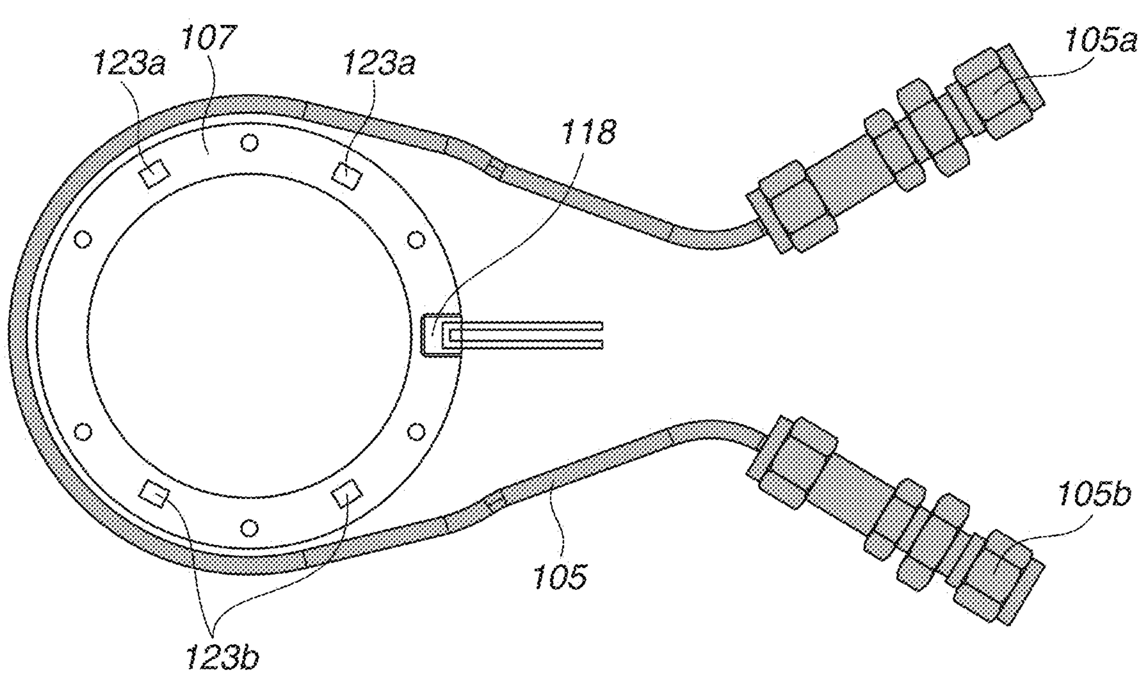
FIG. 10 illustrates an arrangement of the illumination system of the cell detaching apparatus according to exemplary embodiments of the present disclosure.

FIG. 10 illustrates a state where the LED lights 123 are mounted inside the vibration tub 107 made of transparent polycarbonate. The plurality of the LED lights 123 is arranged such that the LED light 123*b* is disposed on the side opposite to the LED light 123*a* to prevent the cells from being shadowed when illuminated.

Figure 14:
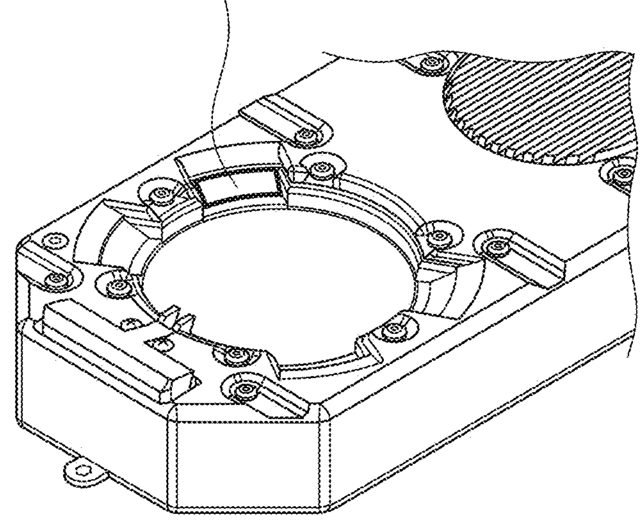
FIG. 14 illustrates an indicator form of the cell detaching apparatus according to exemplary embodiments of the present disclosure.

A ninth exemplary embodiment of the present disclosure will be described below with reference to FIGS. 11 and 14.

Figure 11:
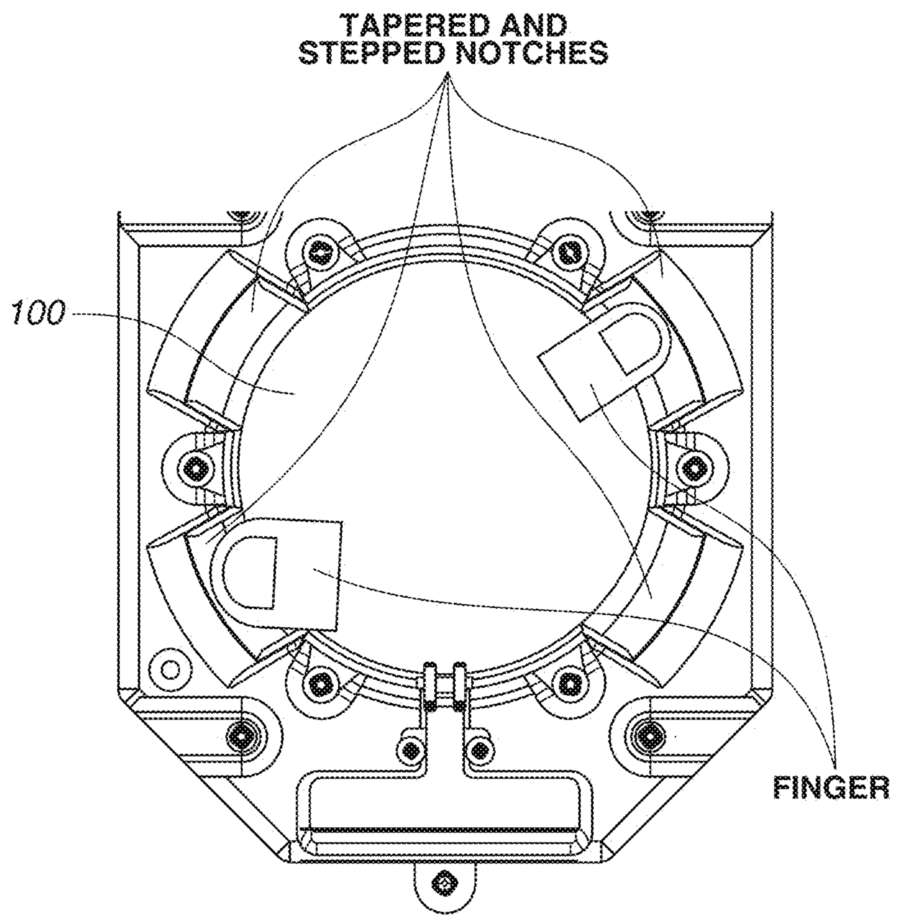
FIG. 11 illustrates steps of the cell detaching apparatus inserted with fingers according to exemplary embodiments of the present disclosure.

As illustrated in FIG. 11, the vibration tub 107 is inserted with fingers to make it easier to take out the culture vessel 100.

A plurality of notches in either one or both of tapered and stepped forms is provided at facing positions. Disposing the notches in tapered or stepped form makes it easier to visually recognize the inside when injecting the fluid volume according to the fifth exemplary embodiment.

A tenth exemplary embodiment of the present disclosure will be described below with reference to FIG. 12.

FIG. 12(1) illustrates an effect when an ultrasonic vibration is applied to the vibration transmission fluid as a heat transfer medium.

FIG. 12(2) (not vibrated) illustrates a surface temperature distribution in a state where the input of the alternating signal to the vibration plate 102 is stopped and where the central part of the dish 100 is subjected to temperature control at around 37° C. by using a thermostatic chamber included in the cell detaching apparatus. FIG. 12(2) illustrates that, in this state, temperature irregularities are formed on the right and left sides of the circular portion where the dish 100 is placed.

An acoustic rectilinear current is known as a fluid movement phenomenon that occurs when an acoustic wave propagates in a fluid. According to the present exemplary embodiment, as a method for solving this issue, the inventors have devised a method for circulating the vibration transmission fluid as a heat transfer medium on the outer bottom of the dish 100 through ultrasonic floating and acoustic rectilinear current. When the dish 100 is floated by the force of the ultrasonic wave, a current of the vibration transmission medium is produced between the bottom of the dish 100 and the vibration plate 102 at the same time. At this timing, the ultrasonic floating provides an effect of preventing the dish 100 from directly receiving the temperature irregularities, and the fluid flow produced by the rectilinear current mixes high- and low-temperature portions. This means that the inventors have devised a method for uniforming the temperature of the dish 100. FIG. 12(1) illustrates a state where the alternating signal is input.

The temperature irregularities disappear on both sides, which means that the entire dish 100 is set at a uniform temperature.

The tenth exemplary embodiment enables providing higher quality cells because of not only stabilizing the amount of energy in the cell detaching but also improved variations of the detaching condition on temperature effects. The present exemplary embodiment also enables providing an ecological, low-price, and easy-to-handle cell detaching apparatus.

An eleventh exemplary embodiment of the present disclosure will be described below with reference to FIG. 13.

Figure 13:
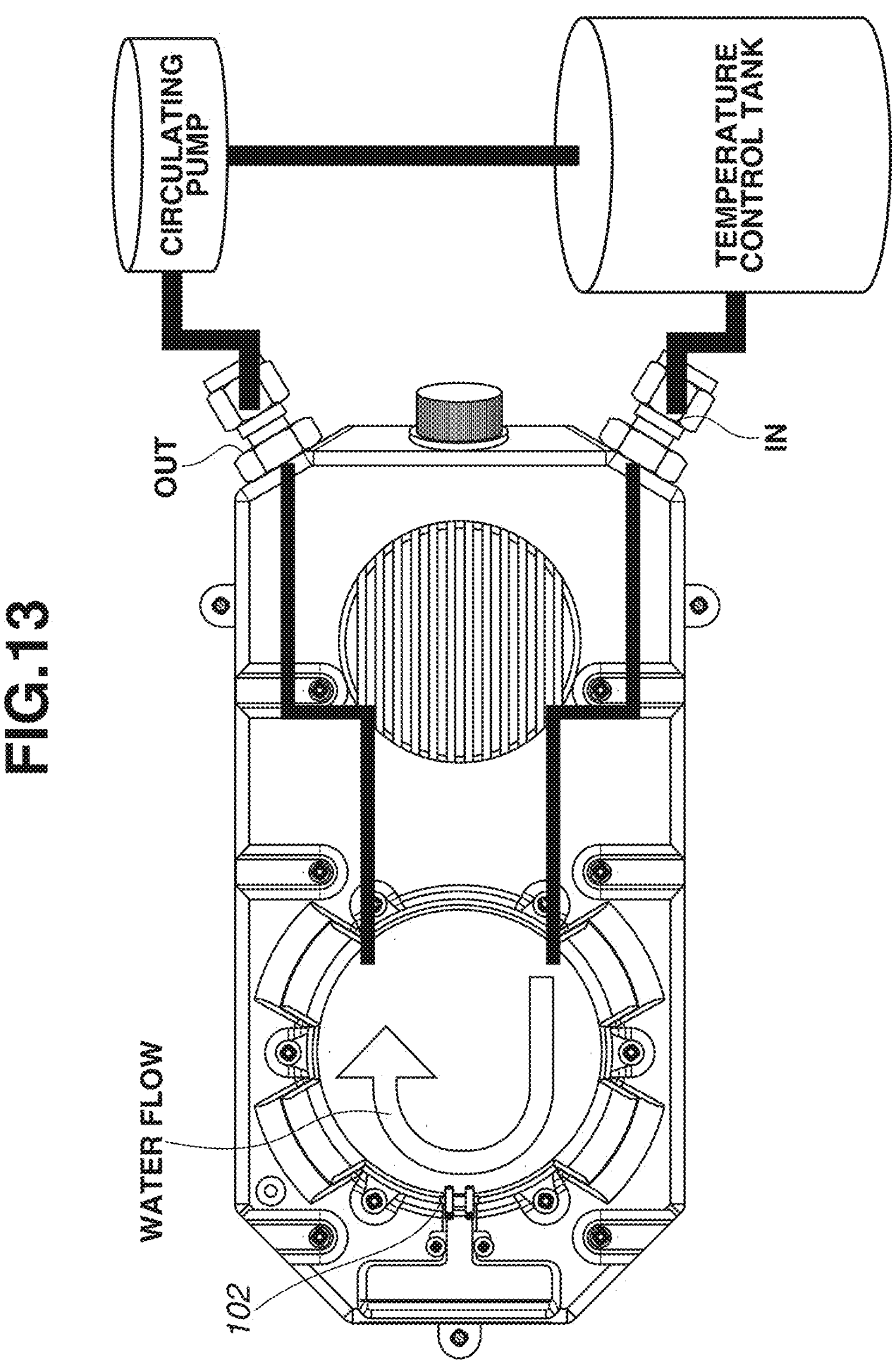
FIG. 13 illustrates a water flow of the cell detaching apparatus according to exemplary embodiments of the present disclosure.

FIG. 13 illustrates the fluid path 111 disposed at a plurality of positions, a flow inlet (IN in FIG. 13), and a flow outlet (OUT in FIG. 13). FIG. 13 also illustrates a method for generating a water flow in the vibration tub 107 so that a constant water flow enters and exits the fluid paths 111 and circulating the vibration transmission fluid under temperature control.

A twelfth exemplary embodiment of the present disclosure will be described below with reference to FIG. 15.

The fluid level (not illustrated) is kept constant at the bottom height of the groove, as described above in the first exemplary embodiment.

However, when the dish 100 is changed to another one with a different size, the suitable water volume may be different. Such a case requires a mechanism for conveniently changing the fluid level to an optional height. The method according to the twelfth exemplary embodiment actively varies the portion of the mountain-like edge line of the fluid path 111 according to the fourth exemplary embodiment. The cell detaching apparatus is configured so that a partition plate (water level adjustment plate) 122 can be replaceably attached at an optionally adjusted height.

As a matter of course, depending on cost and size, the partition plate (water level adjustment plate) 122 may be electrically moved according to a command value from a control circuit for the fluid level adjustment illustrated in FIG. 15.

A thirteenth exemplary embodiment of the present disclosure will be described below with reference to FIG. 18.

Figure 18:
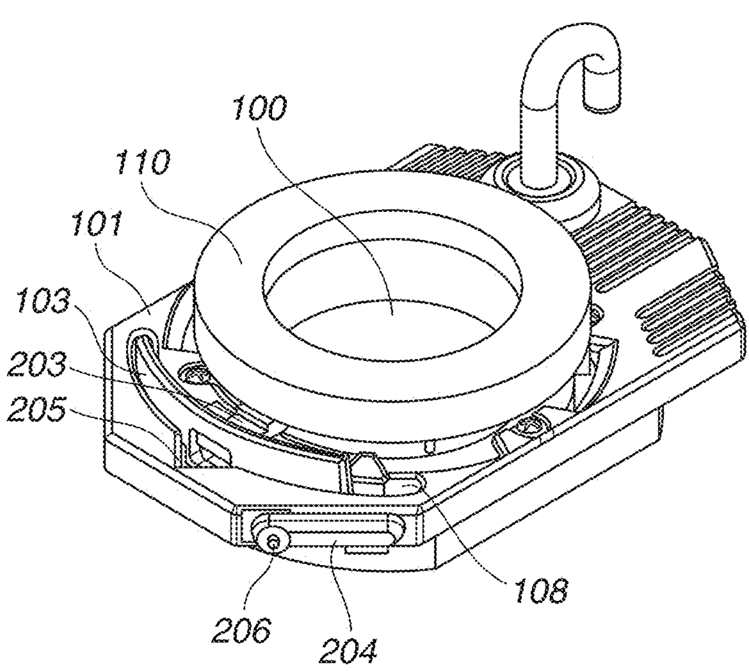
FIG. 18 illustrates a drain form of the cell detaching apparatus according to exemplary embodiments of the present disclosure.

During operation, the vibration transmission fluid is stored in the vibration tub 107 included in the housing 101, and the culture vessel 100 is placed and held down by the weight of the dish weight 110, as illustrated in FIG. 18. FIG. 18 also illustrates a state where the sinking weight 103 is raised, and the vibration transmission fluid is also stored in the storage tub 108. After operation, the vibration transmission fluid is drained off from the cell detaching apparatus 1 and then stored while being kept clean. Therefore, as a method for conveniently draining off the vibration transmission fluid, a storage stand 204 for retaining the drainage posture and a fixing shaft 206 thereof are newly provided. A drain form 205 is disposed to allow the vibration transmission fluid accumulated in the vibration tub 107 and the storage tub 108 to run down from the infundibulum of the housing 101 on the side of the storage tub 108, enabling drainage when the apparatus takes the standing posture.

A fourteenth exemplary embodiment of the present disclosure will be described below with reference to FIG. 19.

Figure 19:
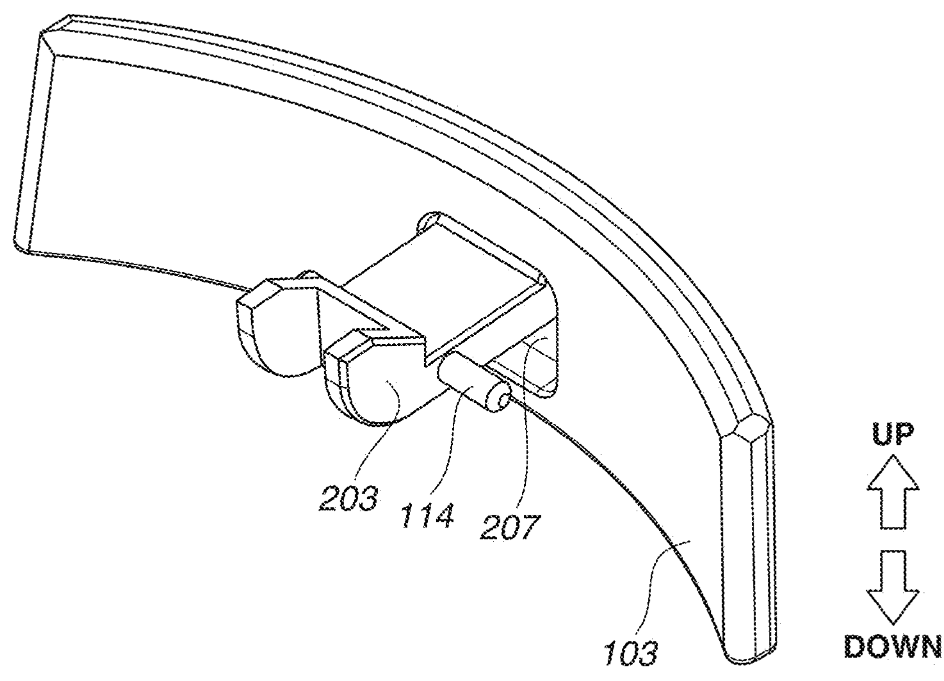
FIG. 19 illustrates a raising and lowering mechanism for the sinking weight of the cell detaching apparatus according to exemplary embodiments of the present disclosure.

The cell detaching apparatus is provided with the movable sinking weight 103, as illustrated in FIG. 19, as a control unit for maintaining a constant height of the fluid level. A unit for moving the sinking weight 103 up and down relates to the present exemplary embodiment. The sinking weight 103 having a through-hole 207 is linearly moved up and down by the action of a sinking weight lever 203 which is rotatable around the rotation center 114. This structure keeps the capacity of the storage tub 108 effective and small in diameter.

Figure 20:
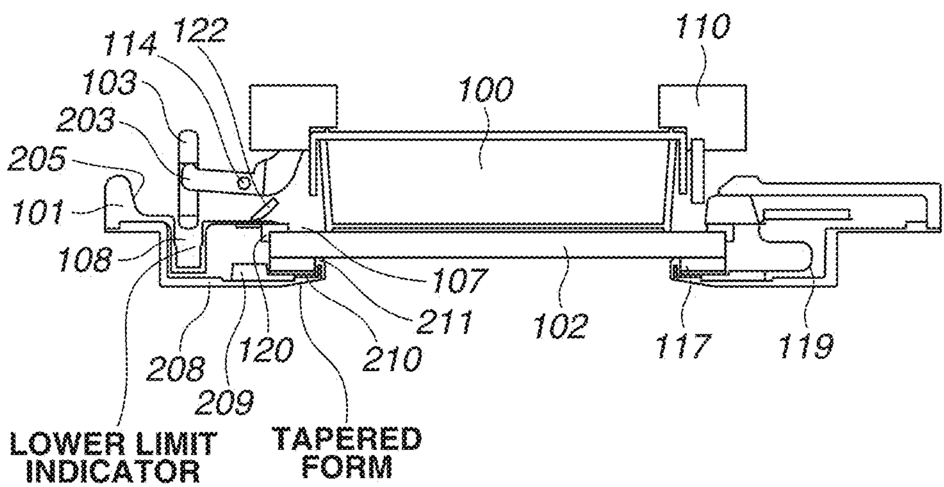
FIG. 20 is a cross-sectional view illustrating the divided sinking weight of the cell detaching apparatus according to exemplary embodiments of the present disclosure.

A fifteenth exemplary embodiment of the present disclosure will be described below with reference to FIG. 20.

The basic configuration of the fifteenth exemplary embodiment is similar to that of the thirteenth exemplary embodiment, and redundant descriptions thereof will be omitted. The through-hole 207 provided at the central part of the sinking weight 103 is hooked in the sinking weight lever 203 which is rotatable around the rotation center 114.

The through-hole 207 at the central part is provided at a position where the movement of the vibration transmission fluid is not disturbed by the drain form 205 connected with the storage tub 108 included in the housing 101. The through-hole 207 at the central part is convenient for collecting the vibration transmission fluid since the sinking weight 103 needs to be kept in balance and arc-shaped.

Figure 21:
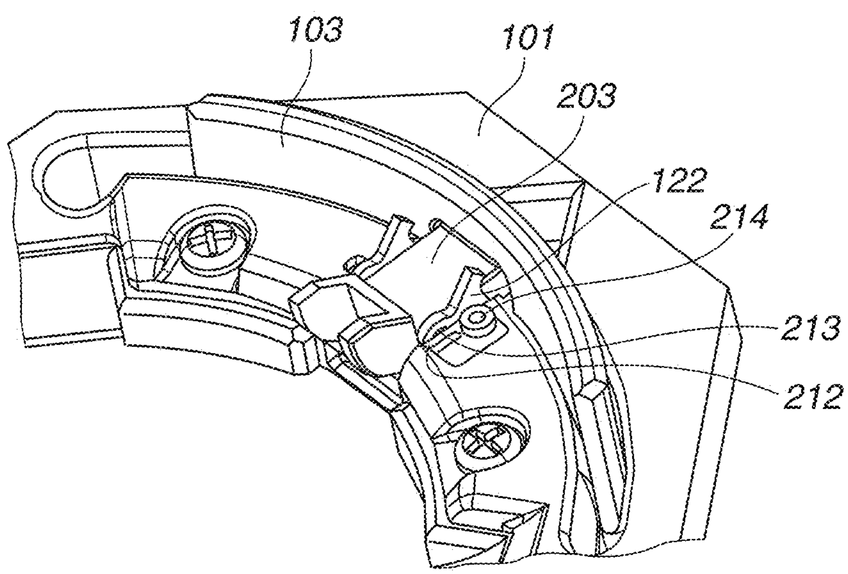
FIG. 21 illustrates a mechanism to optionally adjust a water level of the cell detaching apparatus according to exemplary embodiments of the present disclosure.

A sixteenth exemplary embodiment of the present disclosure will be described below with reference to FIG. 21.

To adjust the water level to an optional height, the apparatus is provided with the partition plate 122 rotatable around the rotation center (not illustrated) of the sinking weight lever 203 of the sinking weight 103 divided by the water path with a variable water level. To prevent the partition plate 122 from unintentionally moving during operation, the partition plate 122 is selectively fixed at a predetermined angle by a latch 212 fastened and fixed to the housing 101 by a fixing screw 214, and a division groove 213 for latch.

To allow selective rotation, the partition plate 122 in the movable weir is provided with a lever.

A seventeenth exemplary embodiment of the present disclosure will be described below with reference to FIGS. 22 and 23.

Figure 22:
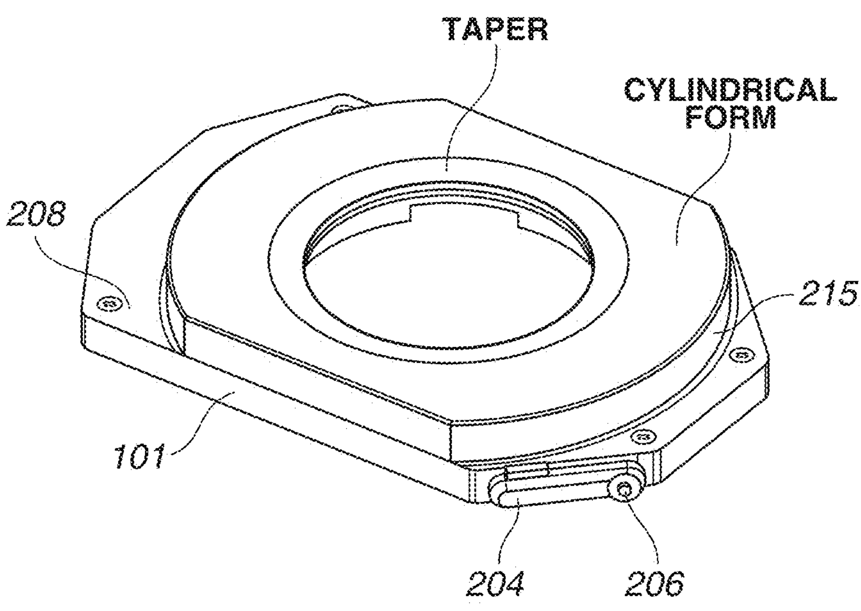
FIG. 22 illustrates an example of a cylindrical projecting portion of the cell detaching apparatus according to exemplary embodiments of the present disclosure.

FIG. 22 is a perspective view illustrating the cell detaching apparatus 1 viewed from the back side. Stages of general microscopes are provided with an observation hole with a diameter from 106 to 110 mm. The stage is configured so that the observation stage surface can be disposed at a position close to an object lens 216. The above-described storage tub 108 of a water level control mechanism is disposed inside a projecting portion 215 and fit into the diameter of the observation hole. A holding unit bottom housing 208 having the projecting portion 215 is provided on the back surface side of the housing 101 so that the cell detaching apparatus 1 becomes level not to incline the base material. Since the projecting portion 215 abuts on the stepped portion, the cell detaching apparatus 1 is kept level.

An eighteenth exemplary embodiment of the present disclosure will be described below with reference to FIG. 23.

Figure 23:
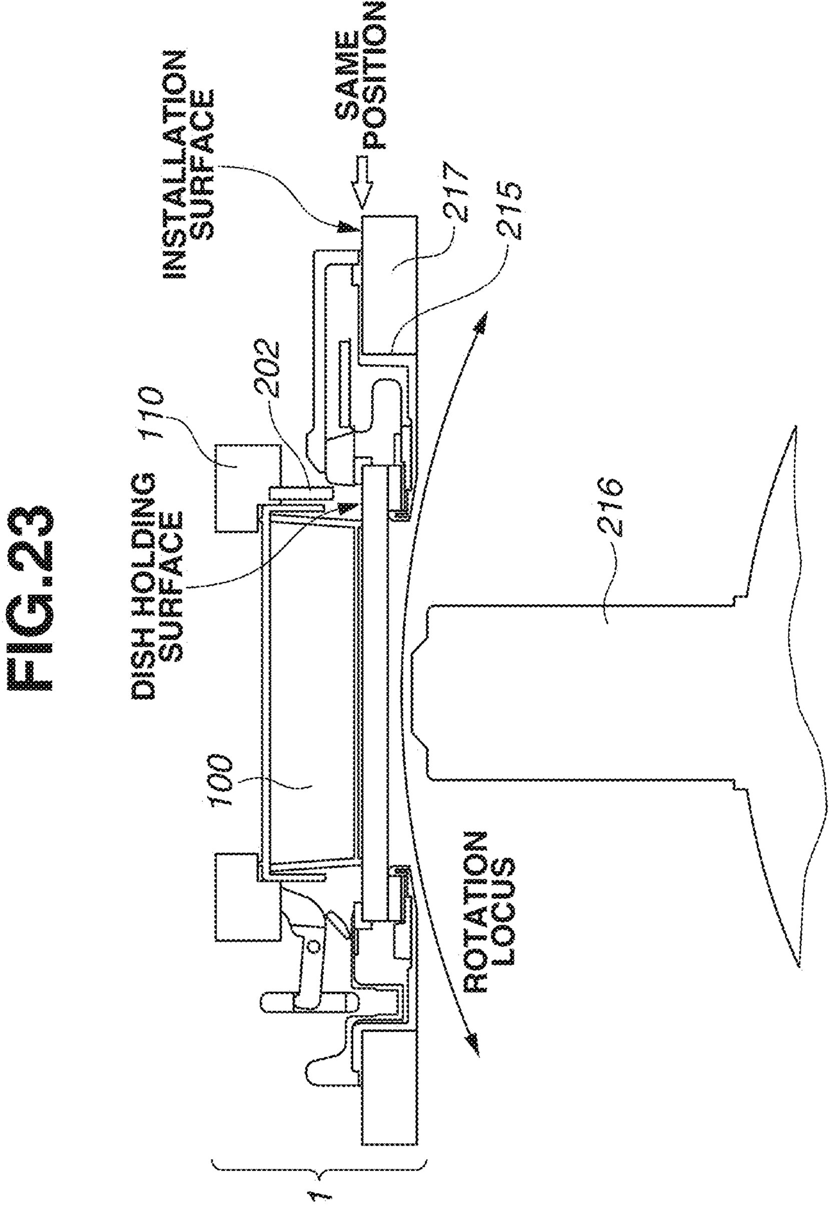
FIG. 23 illustrates the cell detaching apparatus placed on a stage according to exemplary embodiments of the present disclosure.

FIG. 23 illustrates a microscopic table 217. A sample (base material) is generally observed while being placed on the table (stage). The cell detaching apparatus according to the eighteenth exemplary embodiment is devised to observe the sample while being placed on the apparatus. The vibration plate 102 for detaching the cells is disposed under the culture vessel 100 of the base material. The observation procedures have been described above in the seventh exemplary embodiment, and redundant descriptions thereof will be omitted. The eighteenth exemplary embodiment relates not only to a dedicated observation system. As a method applicable to common stand-type microscopes, the object lens 216 attached to a revolver (FIG. 23) moves along the rotation locus illustrated in FIG. 23, stops to be fixed at a correct position, and focuses on the sample. At this timing, the operator observes the sample through the placement surface of the cell culture apparatus 1 and the vibration plate 102 (glass) made of a light-transmitting material. The shape of the apparatus is formed to be embedded in the hole on the common microscopic table (stage) 217. A horizontal stepped portion is formed by intentionally forming the anti-fall projecting portion 215. Further, the vibration plate 102 is formed so that the dish holding surface and the placement surface are at almost the same position (FIG. 23). This enables a series of observation procedures before the cell detaching, during the cell detaching, and after the cell detaching based on the same procedures as regular microscopic observation procedures.

Figure 24:
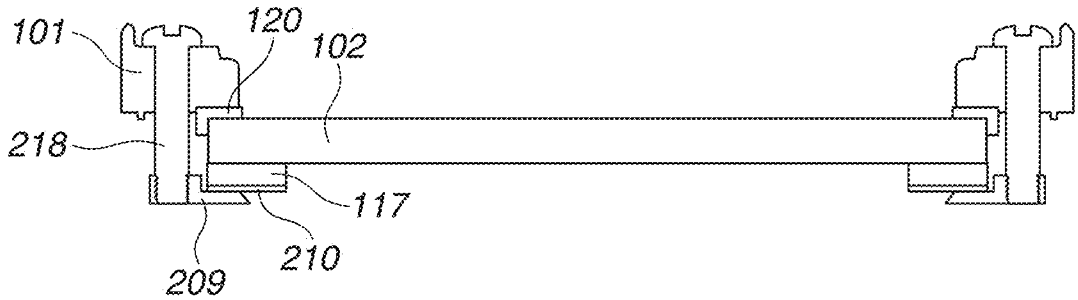
FIG. 24 illustrates a position of a vibrator supporting structure of the cell detaching apparatus according to exemplary embodiments of the present disclosure.

A nineteenth exemplary embodiment of the present disclosure will be described below with reference to FIG. 24.

The vibrator 102 is suspended from the housing 101 by using a plurality of fastening members 218. The vibrator 102 is also suitably supported by a vibration plate supporting member 209 to prevent falling. The vibration plate supporting member 209 is disposed more outward than the average diameter as the neutral axis of the cross-sectional shape of the ring-like piezoelectric element 117. The packing 120 on the top surface is an elastic member having a buffer effect, such as silicon rubber, and is waterproofed. The bottom of the vibrator 102 is levitated as much as possible by a cushioning material (such as felt) 210 containing much air, not to disturb the vibration of the vibrator 102.

Figure 25:
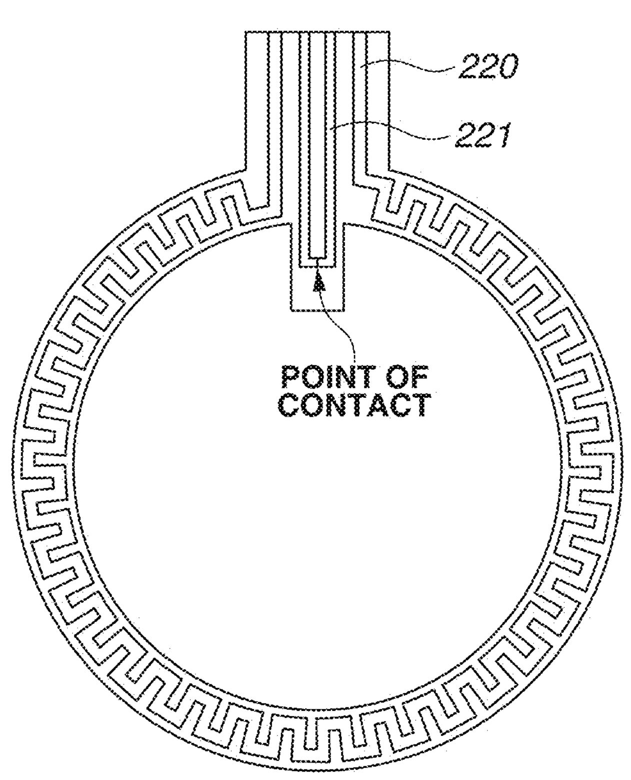
FIG. 25 illustrates an example of a heating wire of the cell detaching apparatus according to exemplary embodiments of the present disclosure.

A twentieth exemplary embodiment of the present disclosure will be described below with reference to FIGS. 25 and 26.

Cell detaching procedures may be performed after the cells are left in a low-temperature environment. A heating unit 219 is provided since the vibration tub 107 needs to be immediately heated to a suitable temperature and subjected to temperature control in order to stabilize the detaching condition. The heating unit 219 including a resistive wire 220 and a thermocouples 118 is packed by a laminate material 221 to make the heating unit 219 thinner and waterproofed, and is firmly fixed to the vibration plate 102 not to disturb the vibration. The resistive wire 220 is patterned in bellows form not to disturb the vibration as much as possible.

A twenty-first exemplary embodiment of the present disclosure will be described below with reference to FIGS. 20, 22 and 23.

The holding unit bottom housing 208 is disposed not to come into contact with the vibration plate supporting member 209.

The object lens 216 illustrated in FIG. 23 moves along the rotation locus (FIG. 23) when the revolver rotates. Therefore, to prevent collision, a taper portion is tapered (FIG. 22) as an example shape for avoiding the rotation locus. The taper shape is circularly provided at the taper portion (FIG. 22). An elastic member such as silicon rubber that does not disturb the vibration is disposed at the inner edge portion. In the event that the object lens 216 interferes the cell detaching apparatus, the elastic member reduces the impact. In the event that the object lens 216 interferes the cell detaching apparatus, the taper portion allows the apparatus to be raised by the force of the revolver to prevent damage to the microscope.

A twenty-second exemplary embodiment of the present disclosure will be described below with reference to FIGS. 18, 27 and 28.

As describe above with reference to FIG. 18, the storage stand 204 for retaining the drainage posture and a fixing shaft 206 thereof are newly provided. The drain form 205 is disposed to allow the vibration transmission fluid accumulated in the vibration tub 107 and the storage tub 108 to run down from the infundibulum of the housing 101 on the side of the storage tub 108, enabling drainage when the apparatus takes the standing posture. The storage stand 204 is a unit for retaining the standing posture.

Figure 27:
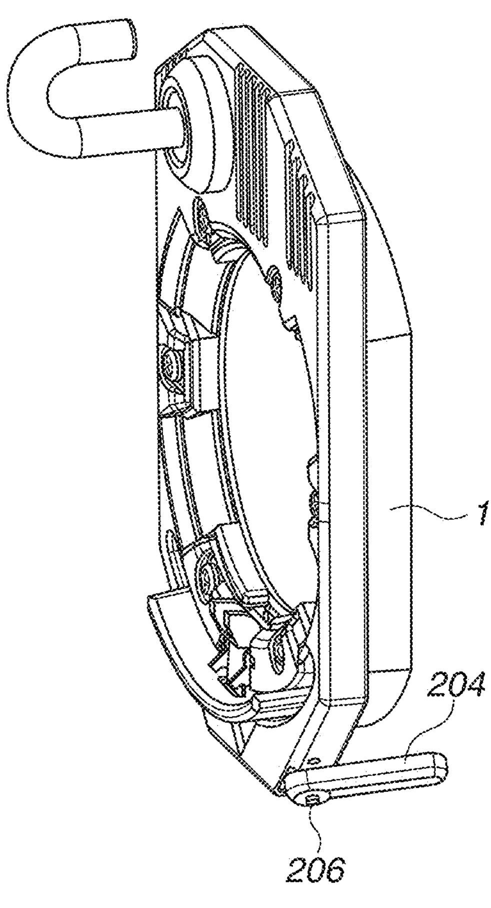
FIG. 27 illustrates an example of a drainage posture of the cell detaching apparatus according to exemplary embodiments of the present disclosure.
Figure 28A:
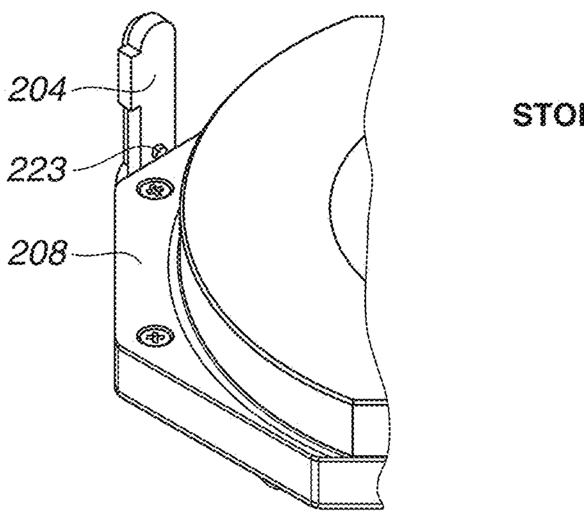
FIGS. 28A to 28B illustrate an example a stand of the cell detaching apparatus according to exemplary embodiments of the present disclosure.

FIG. 27 illustrates the standing posture. FIG. 27 illustrates that the standing posture can be retained when the cell detaching apparatus 1 is supported by the storage stand 204. When the apparatus 1 is to be operated for the cell detaching, the storage stand 204 needs to be stored since it causes an obstruction at the time of placement. Therefore, as illustrated in FIG. 18, the cell detaching apparatus 1 is provided with at least one chamfering portion and no useless projections, improving convenience for storage. The storage stand 204 is rotatably fastened to the housing 101 via a stand fixing shaft 206. When storing the storage stand 204, a convex portion 223 illustrated in FIG. 28A is fit into a concave portion 224 illustrated in FIG. 28B to prevent the storage stand 204 from becoming unsettled. Since the projection of the convex portion 223 needs to be raised at the time of rotation, the stand fixing shaft 206 is made of an elastic member or spring (not illustrated) to be deformable. When the storage stand 204 is used such that the center of gravity of the cell detaching apparatus 1 is positioned more inward than the storage stand placement portion, the storage stand 204 protrudes from the holding unit bottom housing 208. As a matter of course, the chamfering size is almost the same as the size of the storage stand 204.

Figure 28B:
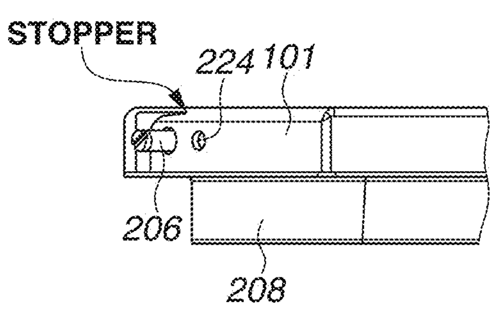

When the storage stand 204 is used, the convex portion 223 is hooked on the stepped portion of the holding unit bottom housing 208 to fix the storage stand 204. Alternatively, another convex portion higher than the convex portion 223 may be provided for use as a stopper. An example is illustrated in FIG. 28B.

The number of storage stand 204 is not limited to one, and a plurality of the storage stands 204 may be provided.

A twenty-third exemplary embodiment of the present disclosure will be described below with reference to FIG. 29.

The cell detaching apparatus according to the twenty-third exemplary embodiment is used with the culture vessel 100 placed in the vibration tub 107. The culture vessel 100 is formed of a culture vessel body 100*a* and a culture vessel cover 100*b*, allowing the cells (FIG. 29) to be taken out from the culture vessel 100. Unfortunately, it is said that cultured cells die or weaken by temperature effects since cells can live only in a limited temperature range. Since the cells (FIG. 29) are cultured in the culture solution (FIG. 29), the temperature of the cells and the temperature of the culture solution (hereinafter referred to as a culture solution temperature) can be recognized to be almost the same. As a unit for fixing the culture vessel 100, for example, a holder made of rubber or spring elastically pinches and holds the culture vessel 100.

Figure 29:
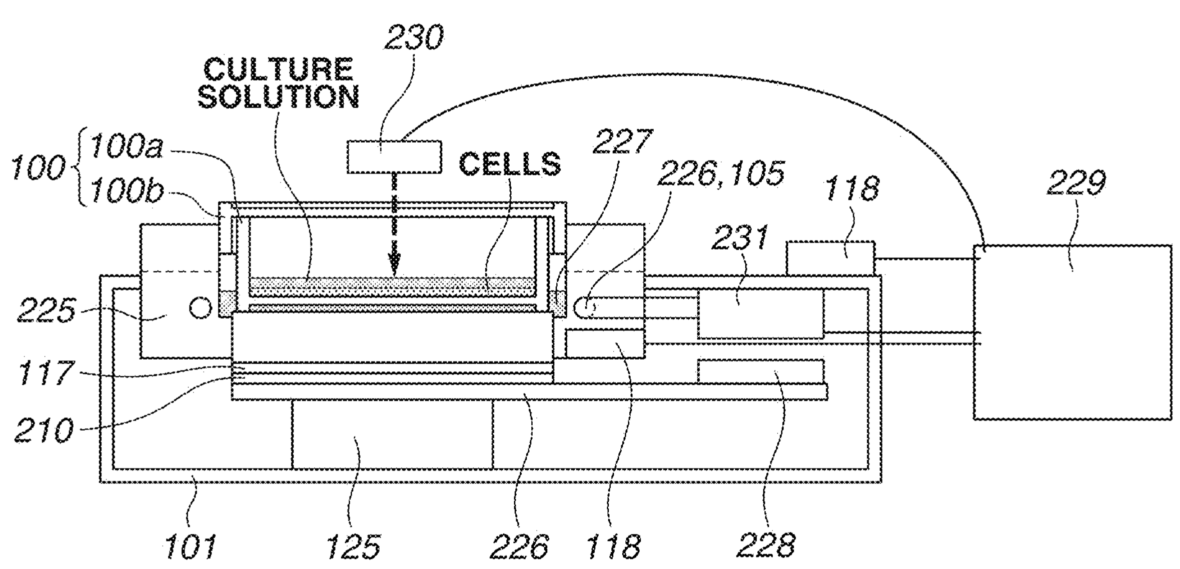
FIG. 29 illustrates a position of a temperature sensor of the cell detaching apparatus according to exemplary embodiments of the present disclosure.

The cell detaching apparatus according to the twenty-third exemplary embodiment illustrated in FIG. 29 includes two thermocouples 118 and a thermo camera 230 as an example form. The thermo camera 230 acquires data of the temperature distribution according to the tenth exemplary embodiment, as illustrated in FIG. 12.

Only the thermocouples 118 provided on a holder 225 may be used. Alternatively, a correction value or correction table calibrated by the thermo camera 230 may be prestored in a memory for temperature control. A correction value may be selected with a circuit such as a Dual-Inline-Package (DIP) switch.

More specifically, the thermo camera 230 monitors the temperature of the culture solution for the purpose of temperature control. The average value of the monitored surface temperature of the culture solution, and the temperature output by the thermocouples 118 (hereinafter referred to as a holder temperature) on the above-described holder 225 relatively change. Since the culture solution temperature and the holder temperature have a correlation, the holder temperature can represent the temperature of the thermo camera 230 based on a constant correction value and an offset correction value.

Similar effects can be obtained even with the temperature output by the thermocouples 118 disposed on the housing 101 (hereinafter referred to as a housing temperature). However, large temperature variations cause accuracy fluctuations.

Figure 26:
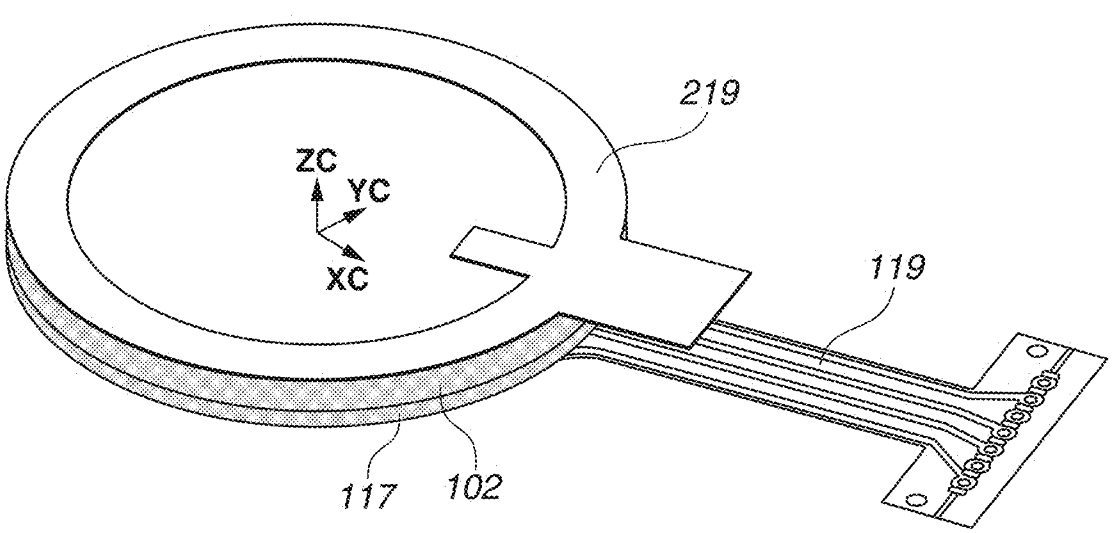
FIG. 26 illustrates an example of a vibrator having the heating wire of the cell detaching apparatus according to exemplary embodiments of the present disclosure.

To perform high-quality temperature control, it is desirable to dispose temperature sensors or the thermocouples 118 on the holder 225 or the vibration plate 102 that abuts on the bottom of the vibration tub 107 illustrated in FIG. 26.

The above-described configuration including at least one thermocouple 118 enables comfortable cell temperature detection.

Since cell temperature detection is possible, a heater 228 and a cooler 231 are provided for the purse of temperature control.

The vibration plate 102 contacts the holder 225, and the vibration plate 102 and the piezoelectric element 117 are firmly fixed. A cushioning material (felt) 210 that does not disturb the insulating performance and vibration is laid on the bottom surface of the piezoelectric element 117. The cushioning material 210 contacts a heat conductive metal 226 to transmit heat to the bottom surface of the platform 125. The heater 228 is placed on the heat conductive metal 226 to superheat the culture solution when it is overcooled.

For cooling, the curved rod of the heat conductive metal 226 is embedded in the holder 225. The rod of the heat conductive metal 226 is fixed to the cooler 231 such as a Peltier element to enable heat transmission. The heat discharge side of the cooler 231 contacts the housing 101 to radiate heat to the atmosphere.

With the above-described configuration, providing at least one thermocouple 118 enables comfortable cell temperature control.

As a supercooling method, a method for connecting the pipe-like heat conductive metal 226 to a chiller is also applicable. As a matter of course, vaporization heat cooling and heat piping are also applicable.

A twenty-fourth exemplary embodiment of the present disclosure will be described below with reference to FIG. 30. FIG. 30 illustrates procedures for controlling the vibration of the vibrator 102 based on sensor information.

Firstly, the operator optionally sets a temperature and detaching time suitable for the detaching of various cells. The temperature is A° C. in FIG. 30. Then, the operator starts the operation of the cell detaching apparatus by touching a button such as a touch panel to activate the cooler 231. Then, the operator loads the temperature of the thermocouples 118 according to the twenty-third exemplary embodiment (B° C. in FIG. 30) and compares the loaded temperature with the preset temperature (A° C.). When A<B, the operator returns to the temperature comparison while continuing cooling. When A>B, due to overcooling, the operator stops the cooler 231, activates the heater 228, and returns to the temperature comparison. When A=B, i.e., when the temperature suitable for detaching various cells is reached, the operator starts the detaching vibration. The suitable temperature refers to a temperature at which the survival rate and freshness of various cells are favorable based on the detaching conditions prechecked by using various types of dishes. This temperature is intended to minimize the detaching force applied to the cells. Meanwhile, the operator constantly controls the cooler 231 and the heater 228 to maintain a constant temperature. In T seconds, the operator stops the vibration and ends the operation.

A twenty-fifth exemplary embodiment of the present disclosure will be described below with reference to the flowchart in FIG. 31. While cells die or weaken by temperature, the vibration plate 102 and the piezoelectric element 117 for producing the detaching vibration have a loss and therefore may be accompanied by heat generation. Therefore, if the heat generated by loss exceeds the radiation capacity of the housing 101 and heat generation occurs, the operator not only turns the heater 228 OFF on the high temperature side but also stops the vibration at the time of temperature determination. Other factors are similar to those for the twenty-fourth exemplary embodiment, and redundant descriptions thereof will be omitted.

A twenty-sixth exemplary embodiment of the present disclosure will be described below with reference to the flowchart in FIG. 32.

Figure 32:
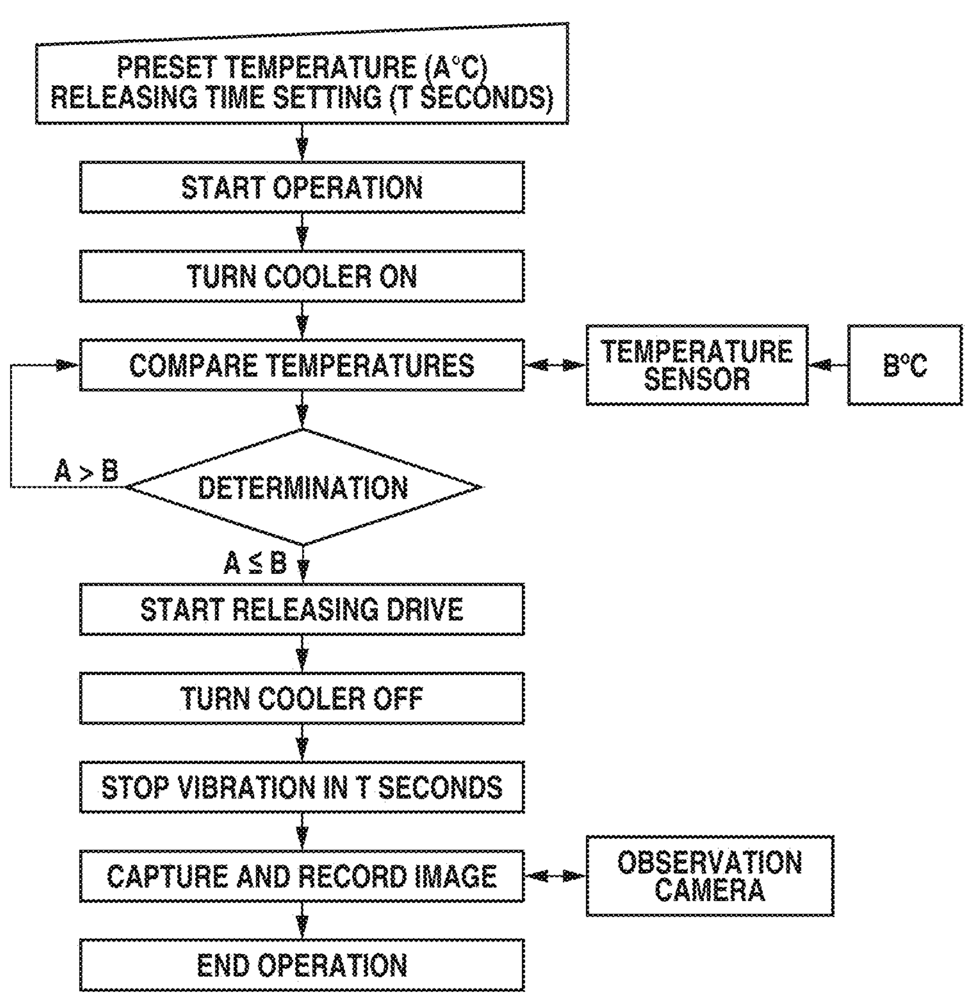
FIG. 32 is a flowchart illustrating an example of cooling temperature control processing of the cell detaching apparatus according to exemplary embodiments of the present disclosure.

FIG. 32 illustrates a case in a general temperature-controlled laboratory or operating room where the cooling temperature setting is equal to or lower than the environmental temperature (normal temperature). This case indicates that the heater 228 for heating according to the twenty-third exemplary embodiment illustrated in FIG. 29 is not required. In this control, after cooling to the initially set preset temperature A° C. or below, the vibration is generated for T seconds. After completion of the cell detaching procedures, the state of the cells immediately after the detaching can be captured and recorded for the purpose of cell quality control.

Figure 33:
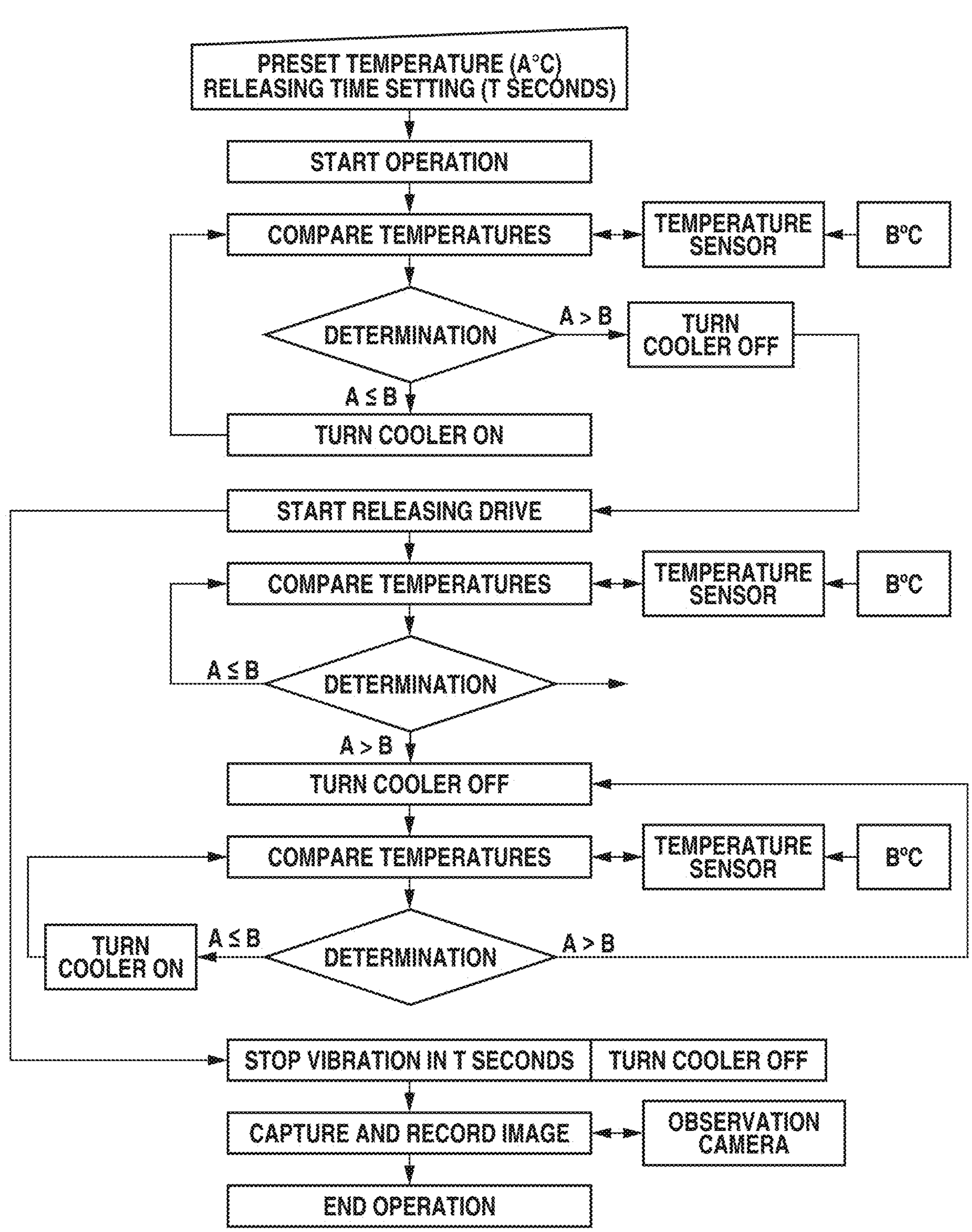
FIG. 33 is a flowchart illustrating cooling control processing of the cell detaching apparatus according to exemplary embodiments of the present disclosure.

A twenty-seventh exemplary embodiment of the present disclosure will be described below with reference to the flowchart in FIG. 33.

After the operation is started, when the sensor temperature B° C. reaches the preset temperature A° C. (target value) or above, the operator turns the cooler 231 ON. When the sensor temperature B° C. falls below the preset temperature A° C., the operator turns the cooler 231 OFF and then starts the detaching operation.

The operator continues temperature control while comparing the temperatures A° C. and B° C. to maintain a constant temperature independently of the vibration.

In T seconds as the irradiation time setting value, the detaching vibration automatically stops, and the cooler 231 stops at the same time.

The operator captures an image of the state of the cells at the end of vibration, and ends the operation.

Figure 34:
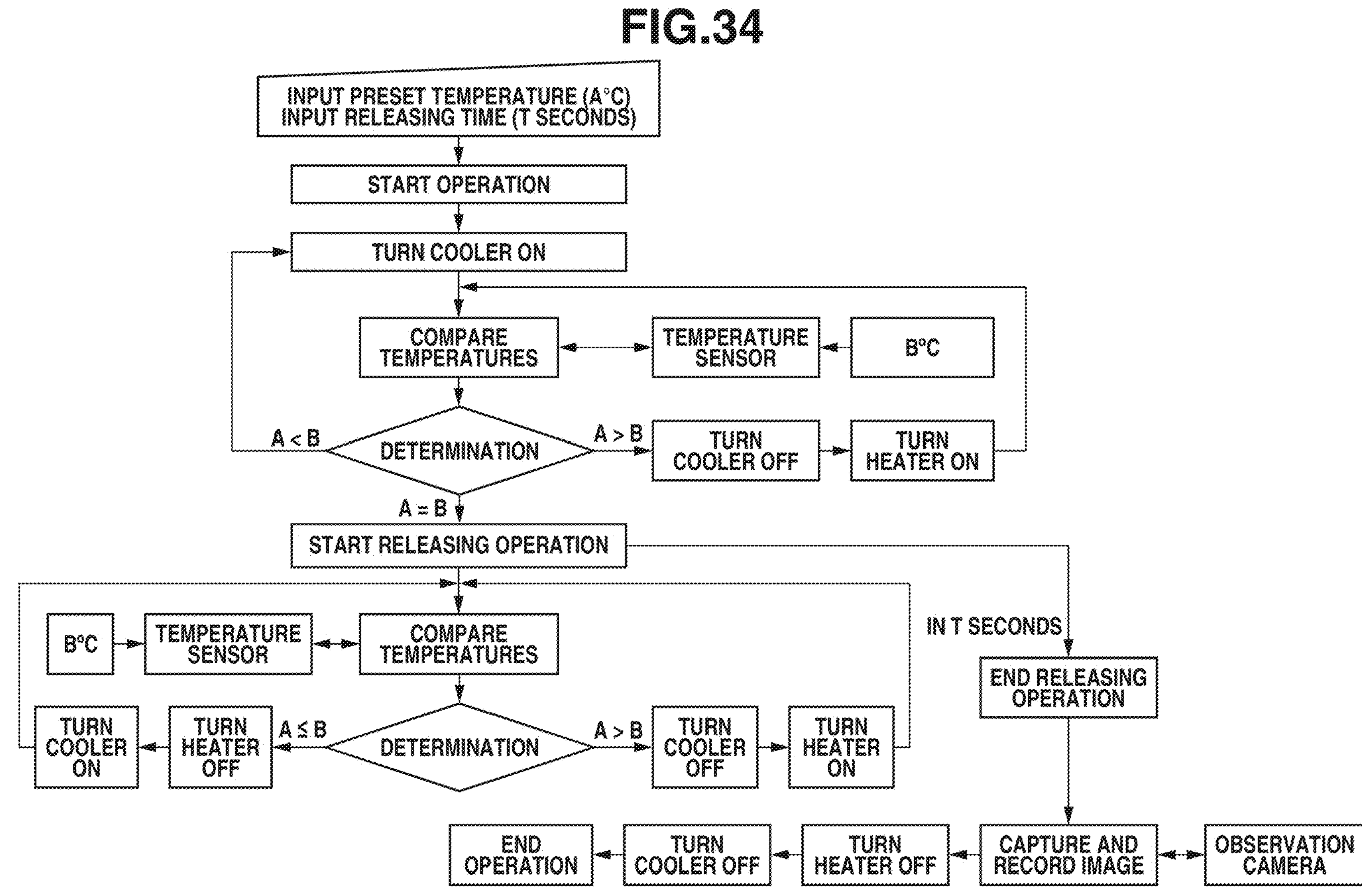
FIG. 34 is a flowchart illustrating heating control processing of the cell detaching apparatus according to exemplary embodiments of the present disclosure.

A twenty-eighth exemplary embodiment of the present disclosure will be described below with reference to the flowchart in FIG. 34.

The twenty-eighth exemplary embodiment indicates that temperature control can be performed by using the heater 228 based on sensor information.

The heater 228 is added to the twenty-eighth exemplary embodiment to improve the temperature control accuracy.

The present exemplary embodiment indicates that the heat quantity variation can be increased by turning the heater 228 ON when the cooler 231 is OFF or turning the heater 228 OFF when the cooler 231 is ON.

A twenty-ninth exemplary embodiment of the present disclosure will be described below with reference to FIG. 29.

The vibration tub 107 includes the holder 225 and the vibration plate 102. The holder 225 contacts the housing 101, and heat transmits to the atmosphere so that the temperature of the vibration plate 102 balances with the ambient temperature. The heat of the vibration plate 102 transmits to the platform at the bottom of the housing 101 via the heat conductive metal 226, and therefore transmits to the microscopic stage or desk to achieve a temperature balance. In this case, the air accumulated between the culture vessel 100 and the holder 225 disturbs smooth heat transmission. According to the twenty-ninth exemplary embodiment, the culture vessel 100 is disposed in the vibration tub 107. In addition, the culture vessel 100 is brought into close contact with the holder 225 included in the vibration tub 107, and the surface of the vibration plate 102 comes into close contact with the vibration transmission substance 227, thus achieving smooth heat transmission. In the configuration in FIG. 18, since the heat of the dish weight 110 transmits to the atmosphere to achieve a temperature balance, the degree of close contact with the dish weight 110 may be further increased.

A thirtieth exemplary embodiment of the present disclosure will be described below with reference to FIG. 29.

The thirtieth exemplary embodiment indicates that the water tube 105 or the heat conductive metal 226 is embedded in the holder 225 to enable directly cooling the vibration transmission substance 227 in the vibration tub 107.

Figure 35:
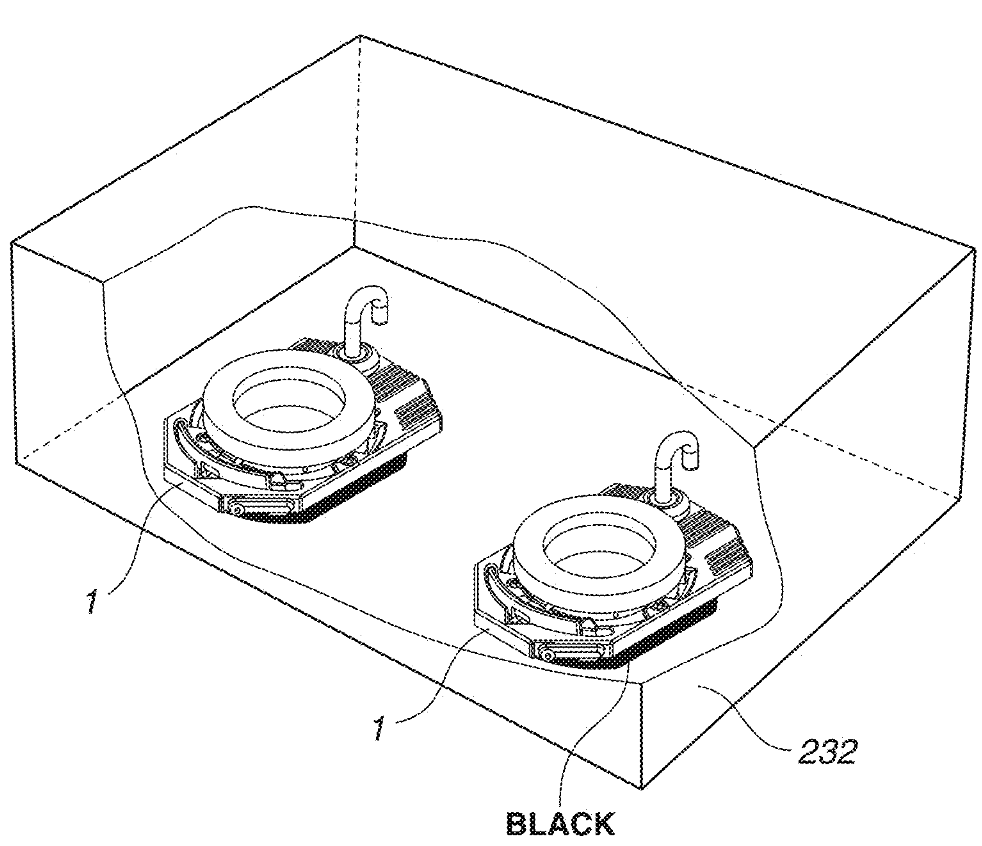
FIG. 35 illustrates an air-conditioning space of the cell detaching apparatus according to exemplary embodiments of the present disclosure.

A thirty-first exemplary embodiment of the present disclosure will be described below with reference to FIG. 35.

The thirty-first exemplary embodiment indicates a state where two cell detaching apparatuses 1 are disposed in a thermostatic chamber 233 as a space where temperature variable control is possible, and indicates that a plurally of the cell detaching apparatuses 1 can be placed according the space size. Since the cell detaching apparatus 1 according to the present exemplary embodiment has a sealed structure, an incubator may be used as the thermostatic chamber 233. In either case, the cell detaching apparatus 1 is often placed on a wire gauze.

According to the thirty-first exemplary embodiment, the cell detaching apparatus 1 is configured to radiate heat by having a bottom surface formed of a thin black material, to achieve smooth heat transmission in the thermostatic chamber 233 and smooth heat radiation to a space. For example, the bottom of the housing 101 is made of aluminum with favorable heat transmission and mat black alumite. This also applies to an example case where the apparatus is disposed on the microscopic table (stage) 217, as illustrated in FIG. 23. FIG. 23 illustrates that no heat-transmitting object is placed at the central part of the microscopic table 217 for the purpose of observation, and indicates the superiority of the present exemplary embodiment.

Figure 36:
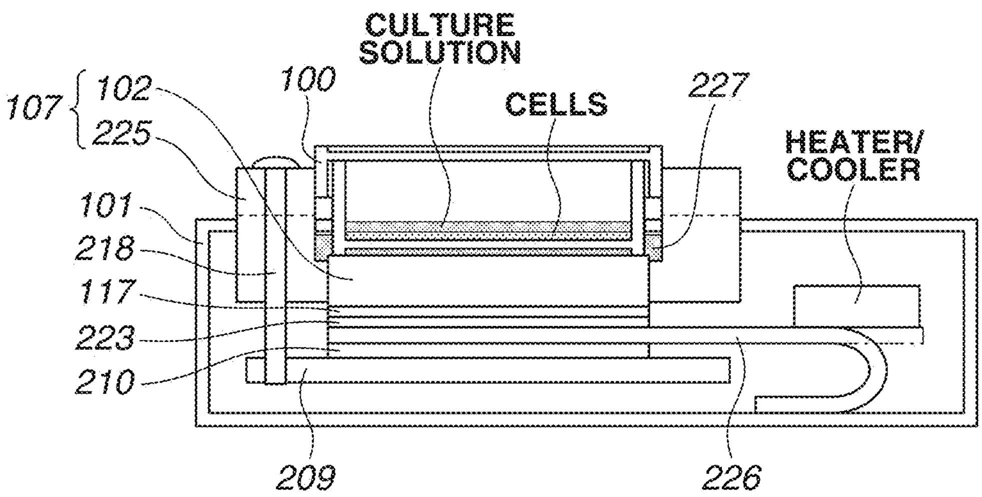
FIG. 36 illustrates an example of heat conduction in the cell detaching apparatus according to exemplary embodiments of the present disclosure.

A thirty-second exemplary embodiment of the present disclosure will be described below with reference to FIG. 36.

Cells are put in the culture solution in the culture vessel 100. The culture vessel 100 contacts the vibration transmission substance 227 in the vibration tub 107 formed of the holder 225 and the vibration plate 102. The bottom surface of the piezoelectric element 117 in contact with the vibration plate 102 is bonded with the heat conductive metal 226 such as a copper foil with an adhesive through a flexible sheet-like film such as an insulation film (polyimide) 227 so as not to disturb the insulation performance and vibration. The heat conductive metal 226 can be directly connected with the housing 101 without using a cushioning material (felt) 210 placed on the vibration plate supporting member 209 suspended by the fastening member 218. Therefore, heat transmits to the lower part of the housing 101. Connecting the heat conductive metal 226 to the heater/cooler illustrated in FIG. 36 facilitates temperature control. The thirty-second exemplary embodiment indicates that heat can be transmitted to locations having a high radiation capacity, increasing the degree of freedom.

Figure 37A:
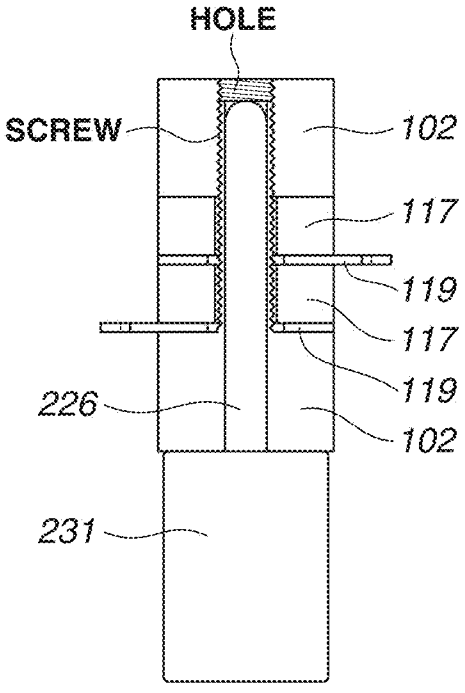
FIGS. 37A and 37B illustrate an example of a heat conduction material for the cell detaching apparatus according to exemplary embodiments of the present disclosure.
Figure 37B:
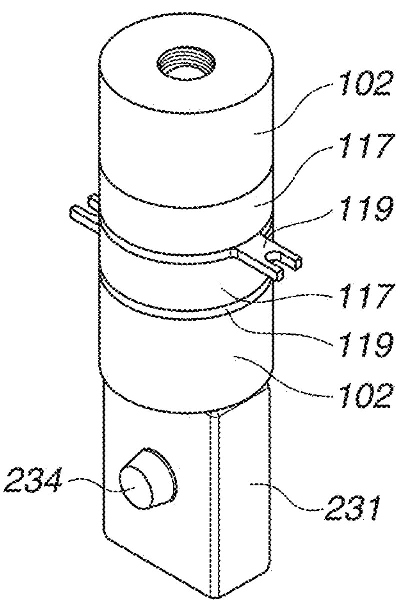

A thirty-third exemplary embodiment of the present disclosure will be described below with reference to FIGS. 37A, 37B, and 38.

There are diverse forms of ultrasonic oscillation apparatuses. FIGS. 37A and 37B illustrate an example of a cooling unit employing a Langevin type ultrasonic transducer. Referring to FIG. 37A, the piezoelectric elements 117 and power supply substrates 119 are alternately sandwiched by the two vibration plates 102 and fixed with a screw. These elements can also be fixed by welding. According to the thirty-third exemplary embodiment, these elements are fastened by a screw form. Referring to FIG. 37A, the vibration plate 102 at the bottom is provided with a male thread, and a hole is formed at the center of the screw rod. The male thread is screwed into the female thread of the upper vibration plate 102. The rod of the heat conduction material 226 for cooling connected with the cooler 231 is inserted into the center hole of the male thread of the vibration plate 102, conveniently cooling the apparatus. This structure enables easily cooling the piezoelectric element 117 which is most likely to generate heat. FIG. 37B is a perspective view illustrating the thirty-third exemplary embodiment of the present disclosure. The structure has been described above with reference to FIG. 37A. FIG. 37B illustrates a temperature control knob 234 that enables manual temperature control for the cooler 231.

Figure 38:
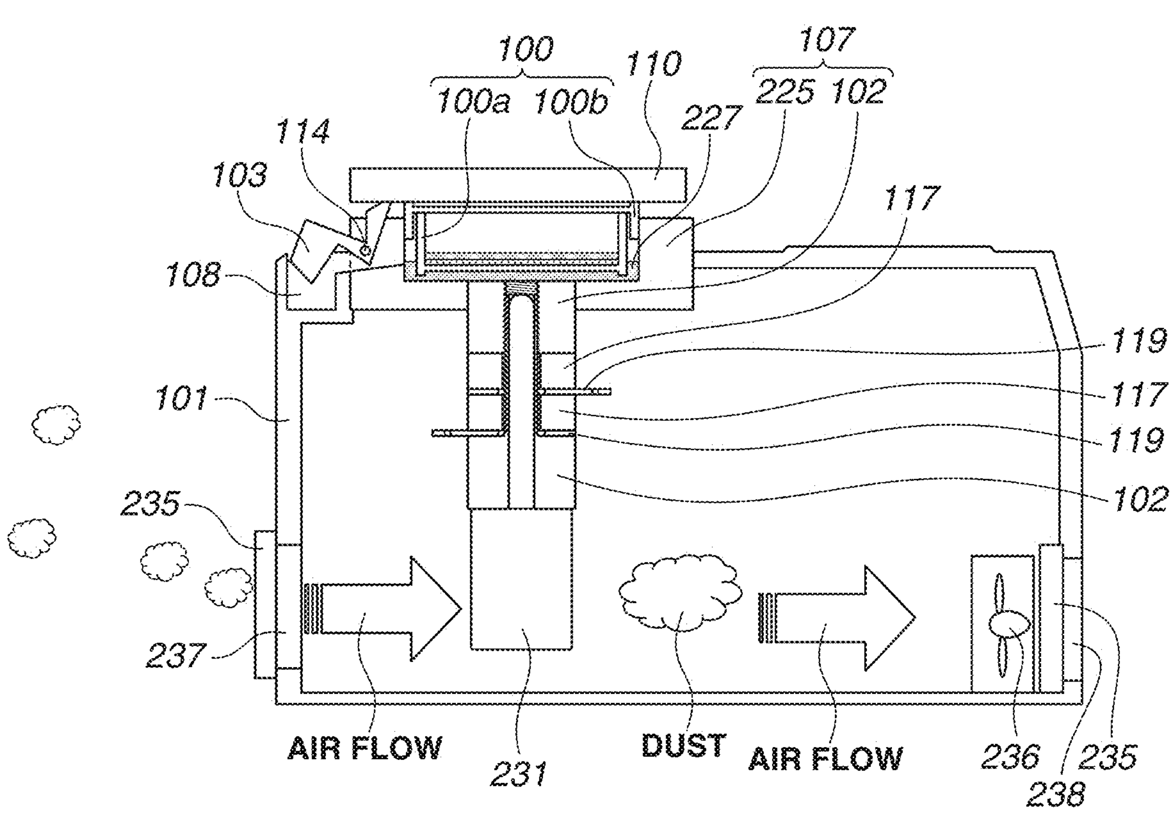
FIG. 38 illustrates an example of the cell detaching apparatus mounting a cooler according to exemplary embodiments of the present disclosure.

FIG. 38 illustrates a configuration of a Langevin type ultrasonic transducer having a water level control mechanism. The housing 101 includes the storage tub 108 and the sinking weight 103 rotatable around the rotation center 114. The dish weight 110 controls the water level of the vibration transmission substance 227 in the vibration tub 107 formed of the holder 225 and the vibration plate 102. The cell detaching apparatus mounts the Langevin type ultrasonic transducer described above with reference to FIGS. 37A and 37B. During the detaching operation, heat exhaust is required because the heat generated by the cooler 231 is blocked in the housing 101. However, since dust drifts in the ambient air, operating the apparatus for a prolonged time period causes even a small amount of dust to be accumulated in the housing 101.

According to the present exemplary embodiment, the apparatus is configured to clean the ambient air and at the same time not to discharge dust in the housing 101 to the outside.

Further, since the cooler 231 is disposed in the housing 101, it is essential to circulate the air in the housing 101 to improve the cooling efficiency. Therefore, a hepa filter 235 is disposed over the entire surface of an intake port 237 to prevent dust from entering the housing 101. This filter is exchangeable for periodical cleaning. Since no dust in the housing 101 is to be scattered to the outside, the hepa filter 235 is also disposed over the entire surface of an exhaust port 238.

A fan 236 is provided in front of the exhaust port 238 to prevent air accumulation in the housing 101, preventing heat accumulation in the cell detaching apparatus 1.

A thirty-fourth exemplary embodiment of the present disclosure will be described below with reference to FIGS. 39A and 39B.

Figures 39A, 39B:
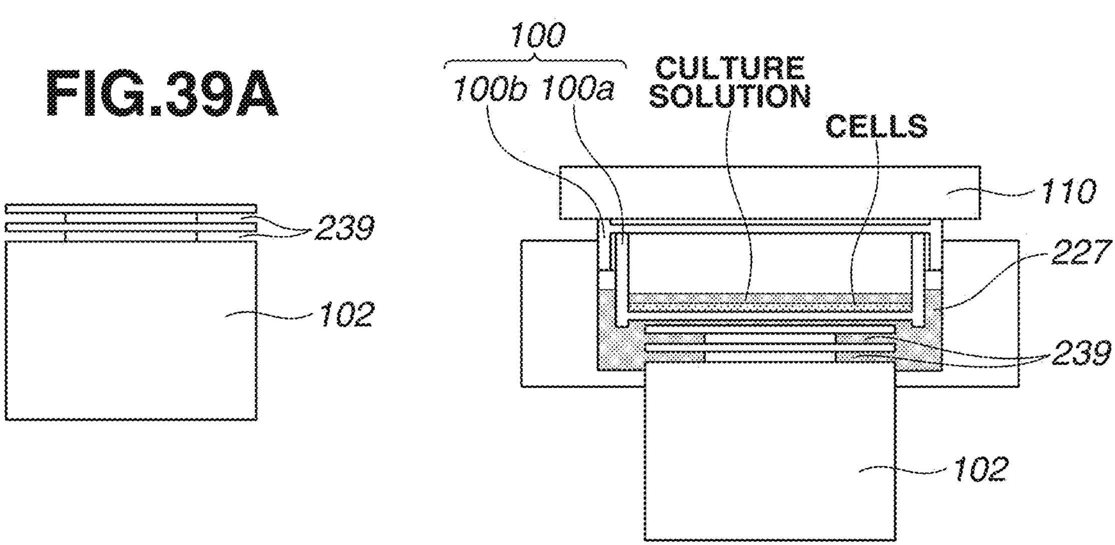
FIGS. 39A to 39B illustrate a concavo-convex shape of the cell detaching apparatus according to exemplary embodiments of the present disclosure.

When a noise vibration is applied to the culture vessel 100 illustrated in FIG. 39B, a characteristic vibration is excited and the culture vessel 100 vibrates. At this timing, heat is generated by the internal friction of materials due to the vibration. According to the thirty-fourth exemplary embodiment, to prevent this heat generation, the vibrator 102 is provided with at least one concavo-convex shaped groove in contact with the vibration transmission substance 227 to allow heat transmission to the vibrator 102 through the vibration transmission substance 227. FIG. 39A illustrates an example of grooves. This configuration promotes heat transmission from the vibration transmission substance 227 to the inside of the vibrator 102. Thus, the apparatus is cooled via a heat conductive material, as illustrated in FIG. 38. The contact between the vibration transmission substance 227 and the vibrator 102 is an important aspect of the present exemplary embodiment because the grooves remarkably increase the close-contact area to increase the heat transmission quantity.

A thirty-fifth exemplary embodiment of the present disclosure will be described below with reference to FIGS. 8 and 40.

The observation window 116 and the observation system have been described above with reference to the seventh exemplary embodiment, and redundant descriptions thereof will be omitted. The thirty-fifth exemplary embodiment makes it possible to observe the cells or a cell sheet inside the culture vessel 100 illuminated by the illumination light of the LED 123, by using an observation system 124 having an image sensor disposed at the top or bottom of the culture vessel 100.

The present exemplary embodiment indicates that the cells are illuminated by the illumination light of the LED 123. This configuration enables the operator to observe the cells or a cell sheet in the culture vessel 100 by using the image sensor provided at the top or bottom of the culture vessel 100. The heat generation by the LED light is smaller than that by a filament bulb. A plurality of the LEDs 123 is embedded in the holder 225, and heat transmits to the holder 225. Therefore, the structure according to the twenty-third exemplary embodiment of the present disclosure is also effective in the present exemplary embodiment. For cooling, the curved rod of the heat conductive metal 226 is embedded in the holder 225. The holder 225 can be cooled since the rod of the heat conductive metal 226 is fixed to the cooler 231 such as a Peltier element to enable heat transmission. Further, based on temperature information for the thermocouples 118, the present exemplary embodiment controls the LED current by using an electric circuit (FIG. 40) as the heater 228 to control the heat quantity. A graphical user interface (GUI), the electric circuit, the vibration mechanism, the thermocouples 118, the LEDs 123, and the power source are electrically connected by electric wires (FIG. 40).

A thirty-sixth exemplary embodiment of the present disclosure will be described below with reference to FIG. 40. In the event that the temperature reaches the thermal death point of cells or that the supercooling prolongs to cause damage to the cells in the cell detaching process, the GUI for the cell detaching (FIG. 40) generates a warning sound (FIG. 40). The thirty-sixth exemplary embodiment indicates that warning display on a monitor is also possible.

A thirty-seventh exemplary embodiment of the present disclosure will be described below with reference to FIG. 40.

The LED 123 has been described above with reference to the eighth exemplary embodiment, and detailed descriptions thereof will be omitted.

Figure 40:
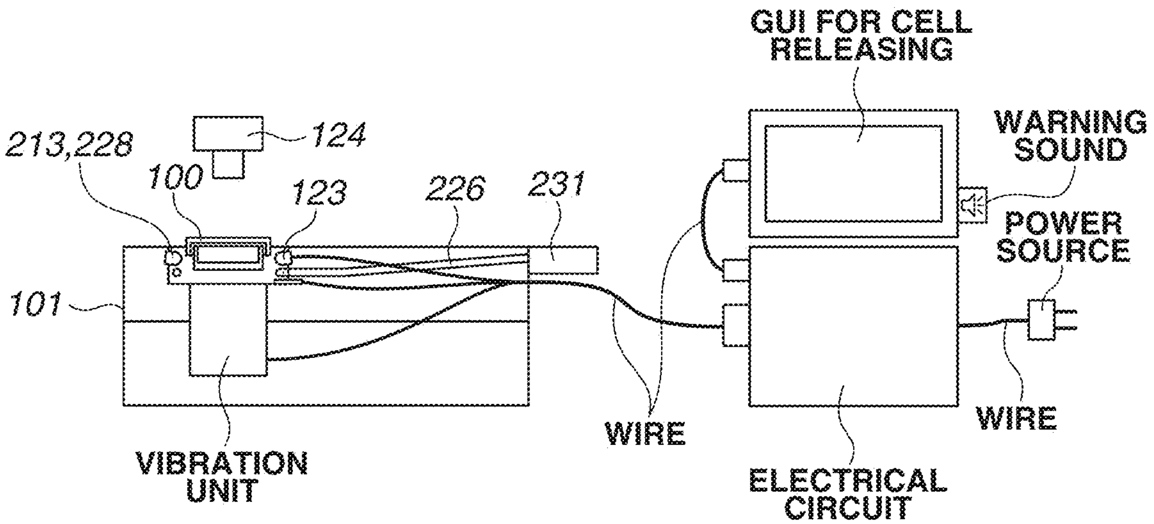
FIG. 40 illustrates examples of a light emitting diode (LED) and a warning sound of the cell detaching apparatus according to exemplary embodiments of the present disclosure.
Figures 41A, 41B:
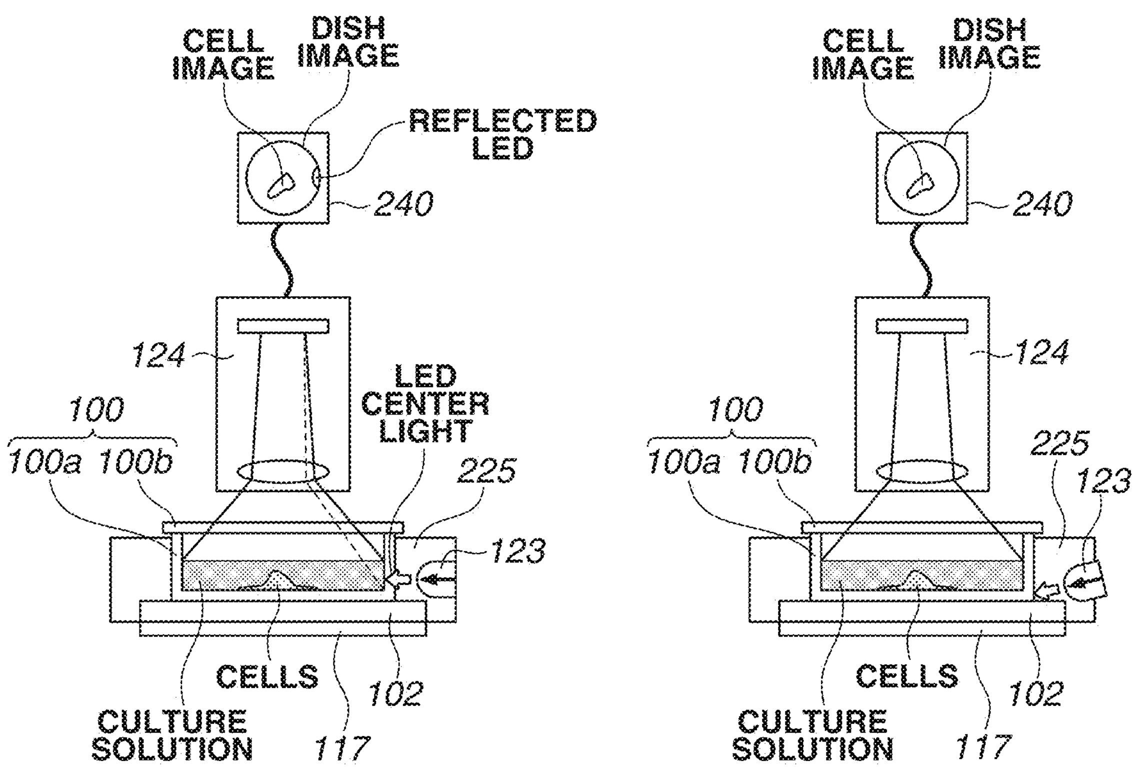
FIGS. 41A and 41B illustrate LED arrangements of the cell detaching apparatus according to exemplary embodiments of the present disclosure.

The thirty-seventh exemplary embodiment indicates a method for preventing the LED 123 from affecting image capturing of the cells (FIG. 40). FIG. 41A illustrates a case where cells are placed at a position where the cells can be irradiated with the highest illumination. The irradiation direction of the LED 123 is indicated by the arrow in FIGS. 41A and 41B. The LED center light having the highest illuminance hits the wall surface of the culture vessel 100, and the image enters the image sensor of the observation system 124. As a result, the light appears in a monitor 240 as the reflected LED in FIG. 41A. Therefore, cells near the edge of the culture vessel 100 cannot be observed.

The inventors have found a position where the LED center light does not hit the wall surface of the culture vessel 100, as illustrated in FIG. 41B.

The LED center light is intense and therefore is reflected at the wall boundary surface of the culture vessel 100. The rectilinear direction of the light indicated by the arrow has the highest intensity. Therefore, the LED center light is intentionally inclined to shift the light from the wall boundary surface of the culture vessel 100 to the side of the piezoelectric element 117. The inventors have found a structure in which the light is not reflected in the monitor 240 in this way. A similar effect can also be obtained by disposing the LED 123 below the bottom surface of a culture vessel 100*a*. However, inclining the LED center light provides remarkable advantages such as the compact size of the circumferential diameter and the reduced thickness in the bottom direction.

The disclosure of the present specification includes the following methods and configurations:

[Configuration 1]

A cell detaching apparatus for detaching cells placed on a base material floating on an acoustic matching liquid, from the base material, the cell detaching apparatus including a holding unit configured to hold the acoustic matching liquid, a detaching unit configured to detach the cells from the base material by applying an ultrasonic vibration to the cells through the acoustic matching liquid, and a control unit configured to perform control to maintain a constant height of a fluid level of the acoustic matching liquid held by the holding unit with respect to the base material during application of the ultrasonic vibration.

[Configuration 2]

The cell detaching apparatus according to configuration 1, further including a vibration tub configured to hold the acoustic matching liquid, and a storage tub configured to store the acoustic matching liquid separately from the vibration tub. The acoustic matching liquid is flowably connected with the storage tub via a fluid path, and the storage tub including a sinking member is configured to control the height of the fluid level of the acoustic matching liquid.

[Configuration 3]

The cell detaching apparatus according to configuration 2, in which a leading end of the sinking member moves down in the storage tub across a rotation center by self-weight.

[Configuration 4]

The cell detaching apparatus according to configuration 2, in which the sinking member is attachable to and detachable from the cell detaching apparatus.

[Configuration 5]

The cell detaching apparatus according to configuration 2, in which the sinking member is stored in the fluid path, and a groove for flowing the acoustic matching liquid is provided on a side opposite to a weight side across the rotation center.

[Configuration 6]

The cell detaching apparatus according to configuration 5, in which the fluid path is provided with a mountain-like edge line.

[Configuration 7]

The cell detaching apparatus according to configuration 2, in which at least either one of the storage tub and the vibration tub is provided with an indicator indicating a fluid volume.

[Configuration 8]

The cell detaching apparatus according to configuration 2, in which the vibration tub is provided with a temperature sensor, and a water tube is disposed around the vibration tub.

[Configuration 9]

The cell detaching apparatus according to configuration 1, further including a circulating pump, a temperature control tank, and a cooling fin for radiating heat larger than a heat quantity generated by driving power for driving the detaching unit.

[Configuration 10]

The cell detaching apparatus according to configuration 1, further including a housing, in which an observation window including a transparent member is provided at a bottom portion of the housing.

[Configuration 11]

The cell detaching apparatus according to configuration 1, further including a light-emitting element disposed inside a vibration tub or inside a housing.

[Configuration 12]

The cell detaching apparatus according to configuration 1, further including a drain form configured to collect and drain off the acoustic matching liquid.

[Configuration 13]

The cell detaching apparatus according to configuration 1, further including a storage stand.

[Configuration 14]

The cell detaching apparatus according to configuration 1, further including a storage tub, a sinking weight vertically movable in the storage tub, and a rotatably separated lever, as a control unit for maintaining a constant height of the fluid level.

[Configuration 15]

The cell detaching apparatus according to configuration 14, in which the sinking weight has an arc shape and is provided with a through-hole rotatably contacting the lever at a central portion.

[Configuration 16]

The cell detaching apparatus according to configuration 1, in which the cell detaching unit includes a movable weir lever configured to selectively and fixably rotate in contact to change a water level of the cell detaching apparatus.

[Configuration 17]

The cell detaching apparatus according to configuration 1, further including a step-like projecting portion for microscopic observation at an outer edge portion, and a projecting portion at a height where a bottom surface of the holding unit substantially coincides with an on-step projecting portion.

[Configuration 18]

The cell detaching apparatus according to configuration 1, further including a vibrator supporting member on the outer side of the average diameter of a ring-like piezoelectric element as a neutral axis of a cross-sectional shape.

[Configuration 19]

The cell detaching apparatus according to configuration 1, further including a temperature sensor in a vibration tub.

[Configuration 20]

The cell detaching apparatus according to configuration 1, further including a heating unit configured to control temperature on a surface of the holding unit.

[Configuration 21]

The cell detaching apparatus according to configuration 1, further including a tapered form on a bottom surface of the holding unit for holding the acoustic matching liquid, and an elastic member made of rubber at a tip of the holding unit.

[Configuration 22]

The cell detaching apparatus according to configuration 1, further including discontinuous portions on an outer edge projecting portion.

[Configuration 23]

The cell detaching apparatus according to configuration 1, further including a temperature sensor for monitoring one or more of a vibrator, a vibration transmission substance, a vessel (dish), and a culture medium (culture solution), as a unit for detecting the cell temperature.

[Configuration 24]

The cell detaching apparatus according to configuration 1, further including a unit configured to control a vibration of a vibrator based on a plurality of pieces of sensor information.

[Configuration 25]

The cell detaching apparatus according to configuration 1, further including a unit configured to stop a vibration when a temperature rises to a predetermined temperature.

[Configuration 26]

The cell detaching apparatus according to configuration 1, further including a unit configured to produce a vibration after cooling to a predetermined temperature or below.

[Configuration 27]

The cell detaching apparatus according to configuration 1, further including a unit configured to control a cooling temperature based on sensor information.

[Configuration 28]

The cell detaching apparatus according to configuration 1, further including a unit configured to control a heating mechanism based on sensor information.

[Configuration 29]

The cell detaching apparatus according to configuration 1, further including a unit configured to perform temperature control by using a water tube and a heat conductive metal in a vibration tub (holder).

[Configuration 30]

The cell detaching apparatus according to configuration 1, further including a housing having a bottom surface formed of a thin black material, and a space for enabling temperature variable control.

[Configuration 31]

The cell detaching apparatus according to configuration 1, further including a piezoelectric element (dielectric material) formed of a heat conductive metal (a flexible copper foil is also applicable) and a thin insulation layer.

[Configuration 32]

The cell detaching apparatus according to configuration 1, further including a cooling rod inside a vibrator.

[Configuration 33]

The cell detaching apparatus according to configuration 1, further including at least one concavo-convex shape on a vibrator of a vibrating member on a vibration tub side so that a vibration transmission substance (vibration transmission fluid) reaches the concavo-convex shape.

[Configuration 34]

The cell detaching apparatus according to configuration 1, further including an observation unit formed of an image sensor disposed at the top or bottom of a vessel of which the inside is illuminated by illumination light of a light emitting diode (LED), the observation unit observing cells or a cell sheet in the vessel.

[Configuration 35]

The cell detaching apparatus according to configuration 1, further including a unit configured to generate a warning sound and display a warning on a monitor.

[Configuration 36]

The cell detaching apparatus according to configuration 1, further including a light emitting element with an optical axis inclined from an upper surface of a vibration plate to a piezoelectric element.

The cell detaching apparatus according to the present exemplary embodiment includes a control unit for maintaining a constant height of the fluid level of the acoustic matching liquid, with respect to the base material, during application of the ultrasonic vibration. This configuration enables reducing variation of the vibration transmitted to the cells during application of the ultrasonic vibration.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Applications No. 2022-013182, filed Jan. 31, 2022, and No. 2022-197059, filed Dec. 9, 2022, which are hereby incorporated by reference herein in their entirety.

What is claimed is:

1. A cell detaching apparatus for detaching cells placed on a base material floating on an acoustic matching liquid, from the base material, the cell detaching apparatus comprising:

a holding unit configured to hold the acoustic matching liquid;

a detaching unit configured to detach the cells from the base material by applying an ultrasonic vibration to the cells through the acoustic matching liquid;

a control unit configured to perform control to maintain a constant height of a fluid level of the acoustic matching liquid held by the holding unit with respect to the base material during application of the ultrasonic vibration; and a storage tub configured to store the acoustic matching liquid separately from the holding unit, wherein the acoustic matching liquid is flowably connected with the storage tub via a fluid path, and the storage tub including a sinking member is configured to control the height of the fluid level of the acoustic matching liquid.

2. The cell detaching apparatus according to claim 1, wherein a leading end of the sinking member moves down in the storage tub across a rotation center by self-weight.

3. The cell detaching apparatus according to claim 1, wherein the sinking member is attachable to and detachable from the cell detaching apparatus.

4. The cell detaching apparatus according to claim 1, wherein the sinking member is stored in the fluid path, and a groove for flowing the acoustic matching liquid is provided on a side opposite to a weight side across the rotation center.

5. The cell detaching apparatus according to claim 4, wherein the fluid path is provided with a mountain-like edge line.

6. The cell detaching apparatus according to claim 1, wherein at least either one of the storage tub and the holding unit is provided with an indicator indicating a fluid volume.

7. The cell detaching apparatus according to claim 1, wherein the holding unit is provided with a temperature sensor, and a water tube is disposed around the holding unit.

8. The cell detaching apparatus according to claim 1, further comprising a circulating pump, a temperature control tank, and a cooling fin for radiating heat larger than a heat quantity generated by driving power for driving the detaching unit.

9. The cell detaching apparatus according to claim 1, further comprising a housing, wherein an observation window including a transparent member is provided at a bottom portion of the housing.

10. The cell detaching apparatus according to claim 1, further comprising a light-emitting element disposed inside the holding unit or inside a housing.

* * * * *